US012575867B2

(12) United States Patent
Teston et al.

(10) Patent No.: US 12,575,867 B2
(45) Date of Patent: Mar. 17, 2026

(54) PECTUS BAR AND STABILIZER DEVICES AND METHODS

(71) Applicant: Zimmer Biomet CMF and Thoracic, LLC, Jacksonville, FL (US)

(72) Inventors: Kevin Lee Teston, Jacksonville, FL (US); Saddy Rodolfo Garcia, St. Augustine, FL (US); Barclay R. Davis, Jacksonville, FL (US); Bryan Wilcox, St. Augustine, FL (US); Nicholas Soroka, Jacksonville, FL (US); Ely Lucus Knowles, Jacksonville, FL (US); T. Shay O'Brien, II, St. Johns, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 48 days.

(21) Appl. No.: 18/597,360

(22) Filed: Mar. 6, 2024

(65) Prior Publication Data

US 2024/0299070 A1 Sep. 12, 2024

Related U.S. Application Data

(60) Provisional application No. 63/450,202, filed on Mar. 6, 2023.

(51) Int. Cl.
*A61B 17/80* (2006.01)
(52) U.S. Cl.
CPC ................................. *A61B 17/8076* (2013.01)
(58) Field of Classification Search
CPC ............ A61B 17/8076; A61B 17/7041; A61B 17/7047; A61B 17/7055; A61B 17/7056; A61B 17/707
See application file for complete search history.

(56) References Cited

U.S. PATENT DOCUMENTS

| | | | |
|---|---|---|---|
| 4,201,215 A | 5/1980 | Crossett et al. | |
| 4,327,715 A | 5/1982 | Corvisier | |

(Continued)

FOREIGN PATENT DOCUMENTS

| | | |
|---|---|---|
| CA | 2076565 A1 | 2/1994 |
| CA | 2733507 A1 | 2/2010 |

(Continued)

OTHER PUBLICATIONS

"International Application Serial No. PCT/US2024/018732, International Preliminary Report on Patentability mailed Sep. 18, 2025", 8 pgs.

(Continued)

*Primary Examiner* — Jacqueline T Johanas
(74) *Attorney, Agent, or Firm* — SCHWEGMAN LUNDBERG & WOESSNER, P.A.

(57) ABSTRACT

A pectus bar assembly can include a first pectus bar and a second pectus bar engageable with a sternum. The pectus bar assembly can also include a first bar link connectable to the first pectus bar and translatable along the first pectus bar and can include a second bar link connectable to the second pectus bar and translatable along the second pectus bar. The pectus bar assembly can also include a bridge defining a longitudinal axis. The bridge can be connectable to the first bar link and the second bar link. The first bar link and the second bar link can be independently translatable along the bridge, and the first bar link and the second bar link can be independently rotatable about the longitudinal axis of the bridge.

20 Claims, 18 Drawing Sheets

(56) References Cited

U.S. PATENT DOCUMENTS

| | | | | |
|---|---|---|---|---|
| 5,092,889 | A * | 3/1992 | Campbell, Jr. | A61B 17/707 606/74 |
| 6,007,538 | A | 12/1999 | Levin | |
| 6,024,759 | A | 2/2000 | Nuss et al. | |
| 6,872,210 | B2 | 3/2005 | Hearn | |
| 6,881,215 | B2 * | 4/2005 | Assaker | A61B 17/7044 606/279 |
| 7,029,472 | B1 * | 4/2006 | Fortin | A61B 17/7014 606/57 |
| 7,156,847 | B2 | 1/2007 | Abramson | |
| 7,229,422 | B2 | 6/2007 | Klobe | |
| 8,333,768 | B2 | 12/2012 | Castro | |
| 8,496,582 | B2 | 7/2013 | Winston | |
| 8,715,285 | B2 | 5/2014 | Lewis et al. | |
| 8,777,952 | B2 | 7/2014 | Bardají | |
| 8,876,823 | B2 | 11/2014 | Li et al. | |
| 9,138,272 | B2 | 9/2015 | Roman et al. | |
| 9,204,899 | B2 * | 12/2015 | Buttermann | A61B 17/707 |
| 9,308,112 | B2 | 4/2016 | Kazerooni et al. | |
| 9,314,285 | B2 | 4/2016 | Reisberg | |
| 9,339,388 | B2 | 5/2016 | Dartevelle | |
| 9,668,792 | B2 | 6/2017 | Roman et al. | |
| 9,743,968 | B2 | 8/2017 | Litch et al. | |
| 9,827,026 | B1 | 11/2017 | Tulenko | |
| 9,833,269 | B2 | 12/2017 | Park | |
| 9,872,708 | B2 | 1/2018 | Park | |
| 10,058,364 | B2 | 8/2018 | Garcia | |
| 10,143,505 | B2 | 12/2018 | Bardají | |
| 10,206,719 | B2 * | 2/2019 | Goel | A61B 17/7032 |
| 10,376,295 | B1 | 8/2019 | Tulenko | |
| 10,531,901 | B2 | 1/2020 | Su | |
| 10,617,455 | B2 | 4/2020 | Maxson | |
| 10,687,875 | B2 * | 6/2020 | Smits | A61B 17/7053 |
| 10,722,279 | B2 | 7/2020 | Balzano et al. | |
| 10,820,931 | B2 | 11/2020 | Garcia et al. | |
| 12,279,797 | B2 * | 4/2025 | Ferro | A61B 17/68 |
| 2002/0143336 | A1 | 10/2002 | Hearn | |
| 2004/0117016 | A1 | 6/2004 | Abramson | |
| 2004/0204713 | A1 | 10/2004 | Abdou | |
| 2005/0049595 | A1 | 3/2005 | Suh et al. | |
| 2005/0240181 | A1 * | 10/2005 | Boomer | A61B 17/7074 606/280 |
| 2006/0058786 | A1 | 3/2006 | Kim et al. | |
| 2006/0074448 | A1 | 4/2006 | Harrison et al. | |
| 2006/0089648 | A1 | 4/2006 | Masini | |
| 2006/0235278 | A1 | 10/2006 | Winston | |
| 2006/0259141 | A1 | 11/2006 | Roman et al. | |
| 2007/0276378 | A1 | 11/2007 | Harrison et al. | |
| 2008/0082101 | A1 | 4/2008 | Reisberg | |
| 2009/0210056 | A1 | 8/2009 | Forsell | |
| 2009/0264933 | A1 * | 10/2009 | Carls | A61B 17/7041 606/264 |
| 2010/0004697 | A1 * | 1/2010 | Fortin | A61B 17/66 606/86 R |
| 2010/0100142 | A1 | 4/2010 | Park | |
| 2010/0137913 | A1 * | 6/2010 | Khatchadourian | A61B 17/7056 606/279 |
| 2010/0256691 | A1 | 10/2010 | Park | |
| 2011/0166612 | A1 | 7/2011 | Bardaji | |
| 2011/0184411 | A1 | 7/2011 | Mckenzie et al. | |
| 2011/0208255 | A1 | 8/2011 | Su | |
| 2011/0251540 | A1 | 10/2011 | Notrica | |
| 2012/0130371 | A1 | 5/2012 | Li et al. | |
| 2013/0204310 | A1 | 8/2013 | Roman et al. | |
| 2013/0211404 | A1 | 8/2013 | Mckenzie et al. | |
| 2014/0135853 | A1 | 5/2014 | Reisberg | |
| 2014/0163691 | A1 | 6/2014 | Dartevelle | |
| 2014/0214103 | A1 | 7/2014 | Roman et al. | |
| 2014/0350613 | A1 | 11/2014 | Bardají Pascual | |
| 2014/0358150 | A1 | 12/2014 | Kaufman et al. | |
| 2015/0080953 | A1 * | 3/2015 | Otte | A61B 17/7004 606/252 |
| 2015/0134009 | A1 | 5/2015 | Licht et al. | |
| 2015/0190174 | A1 * | 7/2015 | McCarthy | A61B 17/7032 606/246 |
| 2015/0190178 | A1 * | 7/2015 | McCarthy | A61B 17/7049 606/279 |
| 2016/0015430 | A1 * | 1/2016 | Buttermann | A61B 17/7032 29/434 |
| 2016/0074078 | A1 | 3/2016 | Roman et al. | |
| 2016/0183981 | A1 * | 6/2016 | Schlaepfer | A61B 17/7056 606/324 |
| 2016/0310262 | A1 | 10/2016 | Doucet et al. | |
| 2016/0367301 | A1 | 12/2016 | Madjarov | |
| 2017/0049554 | A1 | 2/2017 | Li et al. | |
| 2017/0156759 | A1 | 6/2017 | Park | |
| 2017/0238981 | A1 | 8/2017 | Madjarov et al. | |
| 2018/0021074 | A1 | 1/2018 | Smiths et al. | |
| 2018/0228523 | A1 | 8/2018 | Balzano et al. | |
| 2018/0228524 | A1 | 8/2018 | Garcia et al. | |
| 2018/0256227 | A1 | 9/2018 | Maxson | |
| 2018/0303527 | A1 | 10/2018 | Su | |
| 2018/0310973 | A1 | 11/2018 | Son et al. | |
| 2019/0059964 | A1 | 2/2019 | Notrica | |
| 2019/0069938 | A1 | 3/2019 | Martinez-Ferro et al. | |
| 2019/0117272 | A1 * | 4/2019 | Klausman | A61B 17/7052 |
| 2019/0314072 | A1 | 10/2019 | Uemura et al. | |
| 2019/0374267 | A1 | 12/2019 | Madey | |
| 2020/0197058 | A1 | 6/2020 | Maxson | |
| 2020/0315676 | A1 | 10/2020 | Balzano et al. | |
| 2021/0022782 | A1 * | 1/2021 | Martinez Ferro | A61B 17/808 |
| 2021/0212732 | A1 * | 7/2021 | Assaker | A61B 17/7013 |
| 2022/0361933 | A1 * | 11/2022 | Italiaie | A61B 17/8685 |

FOREIGN PATENT DOCUMENTS

| | | | | |
|---|---|---|---|---|
| CA | 2551805 | C | 7/2014 | |
| CA | 3030168 | A1 | 1/2018 | |
| CA | 3054790 | A1 | 9/2018 | |
| CA | 3059921 | A1 | 10/2018 | |
| CN | 217066554 | U | 7/2022 | |
| EP | 583520 | A1 | 2/1994 | |
| EP | 1691702 | A1 | 8/2006 | |
| EP | 2326269 | A1 | 6/2011 | |
| EP | 2326269 | B1 | 10/2013 | |
| EP | 2699180 | A1 | 2/2014 | |
| EP | 2699180 | B1 | 4/2015 | |
| EP | 3612112 | A1 | 2/2020 | |
| EP | 3612112 | A4 | 11/2020 | |
| KR | 20170085280 | A * | 7/2017 | A61B 17/66 |
| KR | 20180023315 | A * | 3/2018 | A61B 17/56 |
| WO | WO-2005055844 | A1 | 6/2005 | |
| WO | WO-2008114915 | A1 | 9/2008 | |
| WO | WO-2009028836 | A2 | 3/2009 | |
| WO | WO-2009028836 | A3 | 5/2009 | |
| WO | WO-2011017962 | A1 | 2/2011 | |
| WO | WO-2013182545 | A1 * | 12/2013 | A61B 17/823 |
| WO | WO-2014153525 | A2 | 9/2014 | |
| WO | WO-2014153525 | A3 | 11/2014 | |
| WO | WO-2015056204 | A1 * | 4/2015 | A61L 27/58 |
| WO | WO-2016130154 | A1 * | 8/2016 | A61B 17/7053 |
| WO | WO-2016188953 | A1 | 12/2016 | |
| WO | WO-2017023147 | A1 * | 2/2017 | A61B 17/8076 |
| WO | WO-2017157802 | A1 | 9/2017 | |
| WO | WO-2018013594 | A1 | 1/2018 | |
| WO | WO-2018037385 | A1 | 3/2018 | |
| WO | WO-2018128089 | A1 | 7/2018 | |
| WO | WO-2018164808 | A1 | 9/2018 | |
| WO | WO-2018195235 | A1 | 10/2018 | |
| WO | WO-2019046626 | A1 | 3/2019 | |
| WO | WO-2019197391 | A1 * | 10/2019 | A61B 17/808 |
| WO | WO-2020106243 | A2 | 5/2020 | |
| WO | WO-2020106243 | A3 | 7/2020 | |

OTHER PUBLICATIONS

"International Application Serial No. PCT/US2024/018732, International Search Report mailed Jul. 4, 2024", 4 pgs.

(56)              References Cited

OTHER PUBLICATIONS

"International Application Serial No. PCT/US2024/018732, Written Opinion mailed Jul. 4, 20 24", 6 pgs.

* cited by examiner

1100

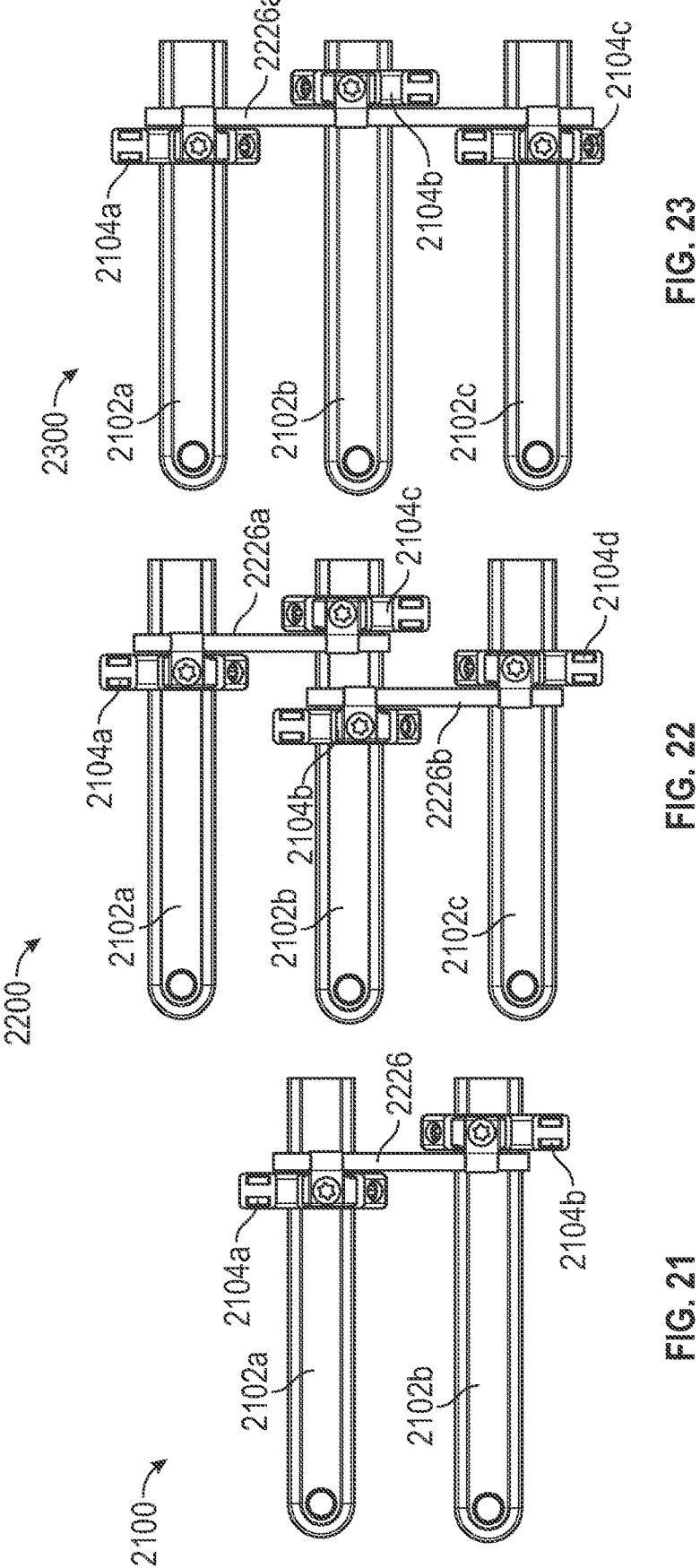

PECTUS BAR AND STABILIZER DEVICES AND METHODS

CLAIM OF PRIORITY

This patent application claims the benefit of priority, under 35 U.S.C. Section 119(e), to first named inventor, Shay O'Brien, U.S. Patent Application Ser. No. 63/450,202, entitled "PECTUS BAR AND STABILIZER DEVICES AND METHODS," filed on Mar. 6, 2023, which is hereby incorporated by reference herein in its entirety.

BACKGROUND

Pectus excavatum and pectus carinatum are conditions affecting a human rib cage which can result from a congenital disorder or injury. In some cases of pectus excavatum and pectus carinatum, physicians install hardware into a patient's ribcage to reshape the ribcage. During a procedure a pectus excavatum correction procedure, one or more pectus bars can be inserted into a thoracic cavity of the patient, at least partially intrathoracically. The bar can then be flipped to force the sternum and rib cage into a proper position, and ends of the bar(s) can be secured to one or more ribs.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 21 illustrates an isometric view of a portion of a pectus bar assembly.

FIG. 22 illustrates an isometric view of a portion of a pectus bar assembly.

FIG. 23 illustrates an isometric view of a portion of a pectus bar assembly.

DETAILED DESCRIPTION

In cases where pectus carinatum or pectus excavatum require surgical correction, a common corrective procedure includes securing a pectus bar to a patient's rib cage to reshape and stabilize the rib cage. This procedure can include the steps of: creating opposing incisions on each side of a patient's rib cage; inserting a curved pectus bar into one incision; weaving the pectus bar through ribs with the concave side of the bar facing the anterior side of the sternum; flipping the pectus bar to push against the anterior side of the sternum to expand the rib cage to a desired shape; securing the pectus bar to the rib cage; securing stabilizers to the pectus bar; securing the stabilizers to the rib cage; and, closing the incisions. Depending on the anatomy of the patient, current hardware solutions may be difficult to secure to a patient's ribs.

In some of these surgical procedures, two pectus bars are used, which can help to keep the sternum in a desired position. Hardware can be used to interconnect the pectus bars and to help prevent the bars from flipping following a procedure. However, the hardware can be relatively cumbersome and time consuming to install, while limiting adjustability. The devices and methods discussed herein can help to address these issues by including a pectus bar bridge that is simple to install and allows for easy adjustment of the pectus bars relative to each other.

For example, a pectus bar assembly can include a first pectus bar and a second pectus bar engageable with a sternum. The pectus bar assembly can also include a first bracket connectable to the first pectus bar and a second bracket connectable to the second pectus bar. The assembly can include a bridge connectable to the first bracket and the second bracket to allow the first bracket and the first pectus bar to translate along the bridge, and to allow the second bracket and the second pectus bar to translate, independently of the first pectus bar, along the bridge.

The above discussion is intended to provide an overview of subject matter of the present patent application. It is not intended to provide an exclusive or exhaustive explanation of the invention. The description below is included to provide further information about the present patent application.

Figure 1:
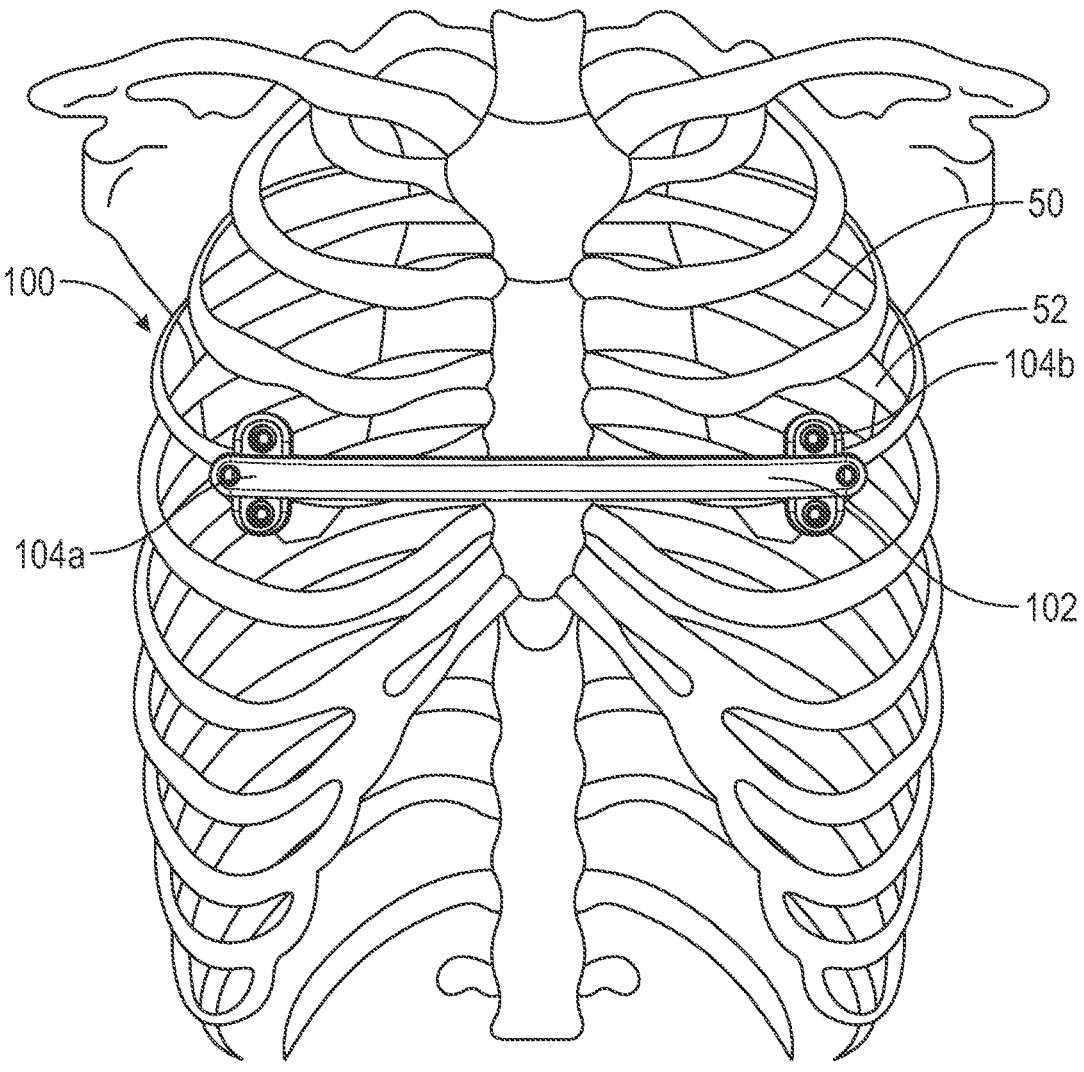
FIG. 1 illustrates an X-ray image of a pectus bar assembly installed in a ribcage of a patient.

FIG. 1 illustrates an X-ray image of a pectus bar assembly 100, which can include a pectus bar 102 and stabilizers 104a and 104b. Also shown in FIG. 1 is ribcage 50, which includes ribs 52. FIG. 1 shows how the pectus bar 102 can be secured to a ribcage along with the stabilizers 104. FIGS. 2-10 discuss additional details of various pectus bar assemblies and procedures.

Figure 2:
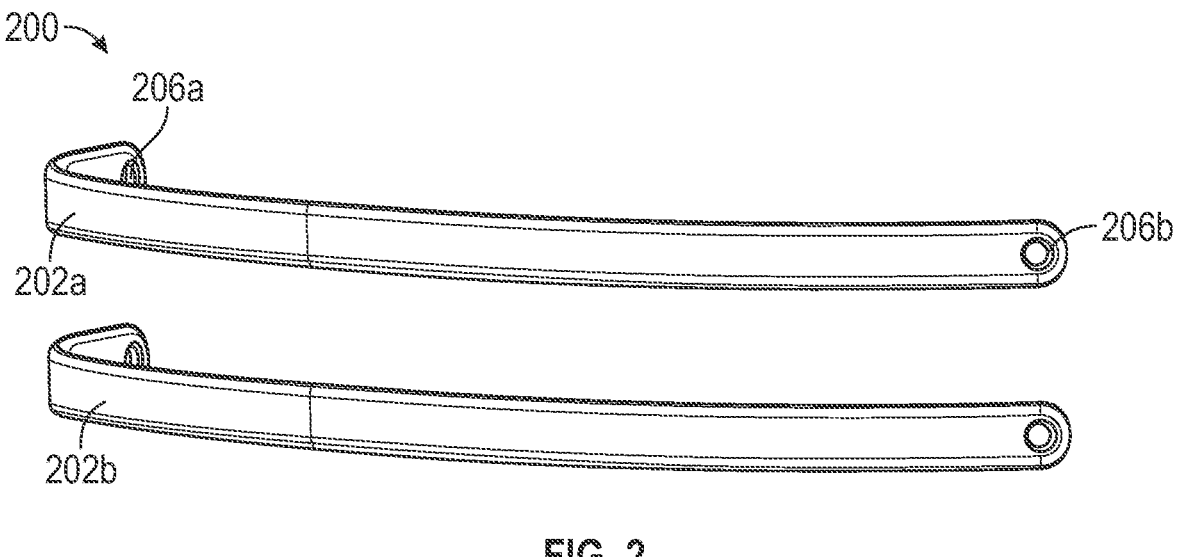
FIG. 2 illustrates an isometric view of a portion of a pectus bar assembly.
Figure 3:
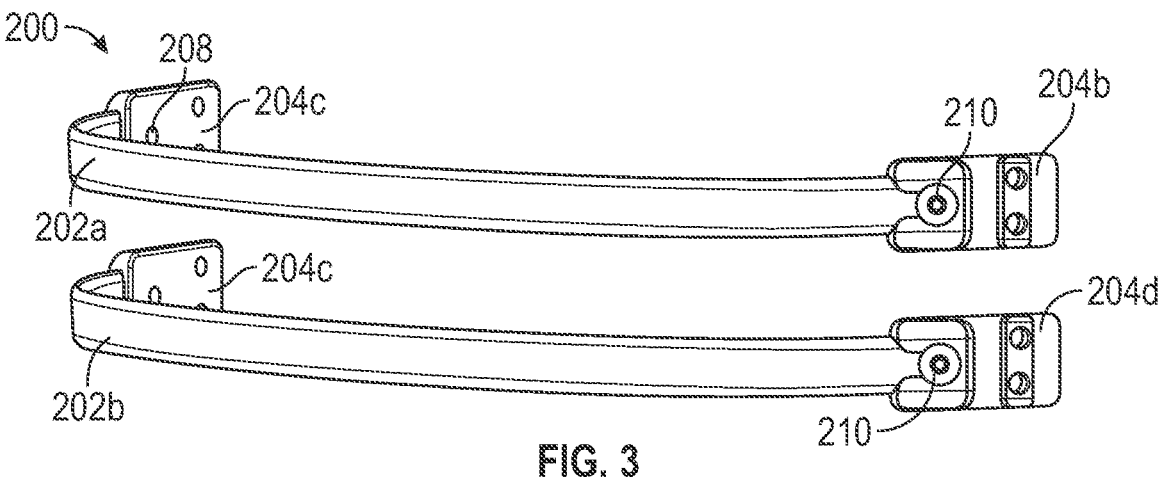
FIG. 3 illustrates an isometric view of a portion of a pectus bar assembly.

FIG. 2 illustrates an isometric view of a portion of a pectus bar assembly 200. FIG. 3 illustrates an isometric view of a portion of the pectus bar assembly 200. FIGS. 2 and 3 are discussed together below. The pectus bar assembly 200 can be similar to the pectus bar assembly 100 discussed above in that the pectus bar assembly 200 can be configured to be installed in a ribcage for correction of pectus excavatum or pectus carinatum. The pectus bar assembly 200 can differ in that the pectus bar assembly 200 can include multiple pectus bars and different hardware. Any of the pectus bar assemblies discussed above or below can be modified to include the features of the pectus bar assembly 200.

The pectus bar assembly 200 can include a pectus bar 202a (e.g., a first pectus bar) and a pectus bar 202b (e.g., a second pectus bar) (collectively referred to as pectus bars 202). Each of the pectus bars 202 can be a rigid or semi-rigid bar constructed of materials such as metals and plastics. For example, the pectus bars 202 can be constructed of biocompatible materials such as one or more of stainless steel alloys, cobalt-chromium, titanium, titanium alloys, polyether ether ketone (PEEK), polyether ketone ketone (PEKK), or the like.

The pectus bars 202 can have an elongate body forming a curve, such as a c-shape, and can be rigid (or semi-rigid) but flexible enough to be bent to match a curvature of a patient's ribcage using tools, such as a bar bender. As shown in FIG. 2, the pectus bars 202 can include bar bores 206a and 206b that can be located near terminations of the pectus bars 202 (e.g., the pectus bar 202a). The bar bores 206 can be configured to receive fasteners, such as bone screws or sutures, such as to secure the pectus bar 202 to ribs and/or soft tissues of ribcage 50. Optionally, the bar bores 206 can be threaded.

As shown in FIG. 3, the pectus bar assembly 200 can include stabilizers or brackets 204a-204d (collectively referred to as stabilizers 204). Stabilizers 204a and 204b can be connected to end portions of the pectus bar 202a and stabilizers 204c can be connected to end portions of the pectus bar 202b, as discussed in further detail below. Each of the stabilizers 204 can be a rigid or semi-rigid component constructed of materials such as metals and plastics. For example, the stabilizers 204 can be constructed of biocompatible such as one or more of stainless steel alloys, cobalt-chromium, titanium, titanium alloys, polyether ether ketone (PEEK), polyether ketone ketone (PEKK), or the like.

FIG. 3 also shows that each of the stabilizers 204 can include a bore 208 configured to receive a fastener 210 at least partially therein. The fastener 210 can extend at least partially into the bar bore 206b and the bore 208 to secure the stabilizers 204b to the pectus bar 202a. The bore 208 can be threaded to connect the fastener 210 to the bore 208 and therefore to the pectus bar 202 and the stabilizer 204. Any of the stabilizers 204 can include such a bore and can be securable to their respective bar bore 206 in a similar way. Further details of the stabilizers 204 are discussed below with respect to FIG. 3A.

Figure 3A:
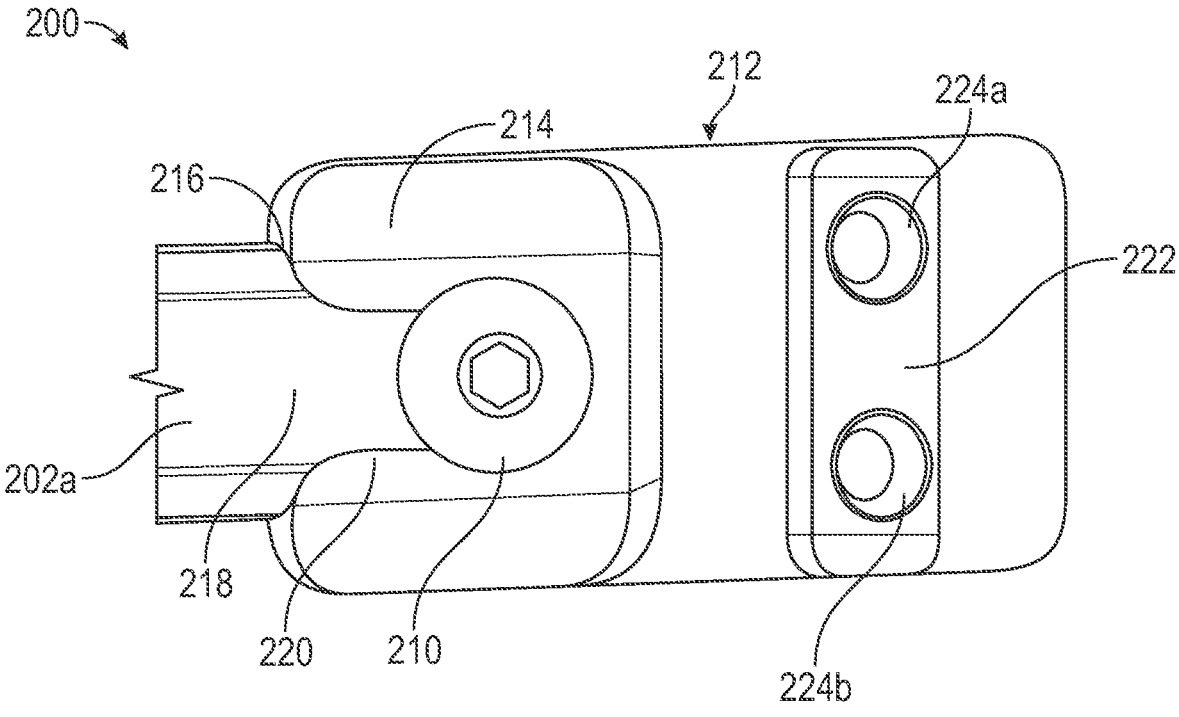
FIG. 3A illustrates an isometric view of a portion of a pectus bar assembly.

FIG. 3A illustrates an isometric view of a portion of the pectus bar assembly 200. The pectus bar assembly 200 of FIG. 3A can be consistent with the pectus bar assembly 200 of FIGS. 2-3 discussed above. FIG. 3A shows additional details of the pectus bar assembly 200. For example, FIG. 3A shows that the stabilizer 204b can include a base 212 and a receiver 214 connected to the base 212. The receiver 214 can define an opening 216 configured to receive an end portion 218 of the pectus bar 202a at least partially therein, such as to align the bar bore 206b with the bore 208 of the stabilizers 204b. The receiver 214 can also include a slot 220. The slot 220 can be configured (e.g., sized or shaped) to allow the fastener 210 and the end portion 218 to be inserted into the receiver 214 when the fastener 210 is connected to the end portion 218 via the bore 206b, which can help to simplify the procedure.

The stabilizer 204b can also include a boss 222 that can extend from a surface of the base 212. The boss 222 define bores 224a and 224b that can be configured (e.g., threaded) to receive fasteners therein, as discussed below. As also discussed below, the boss 222 can be configured (e.g., sized or shaped) to be insertable into a bracket. Though the stabilizer 204b is discussed with respect to FIG. 3A, any of the stabilizers can include the components of the stabilizer 204b.

Figure 4:
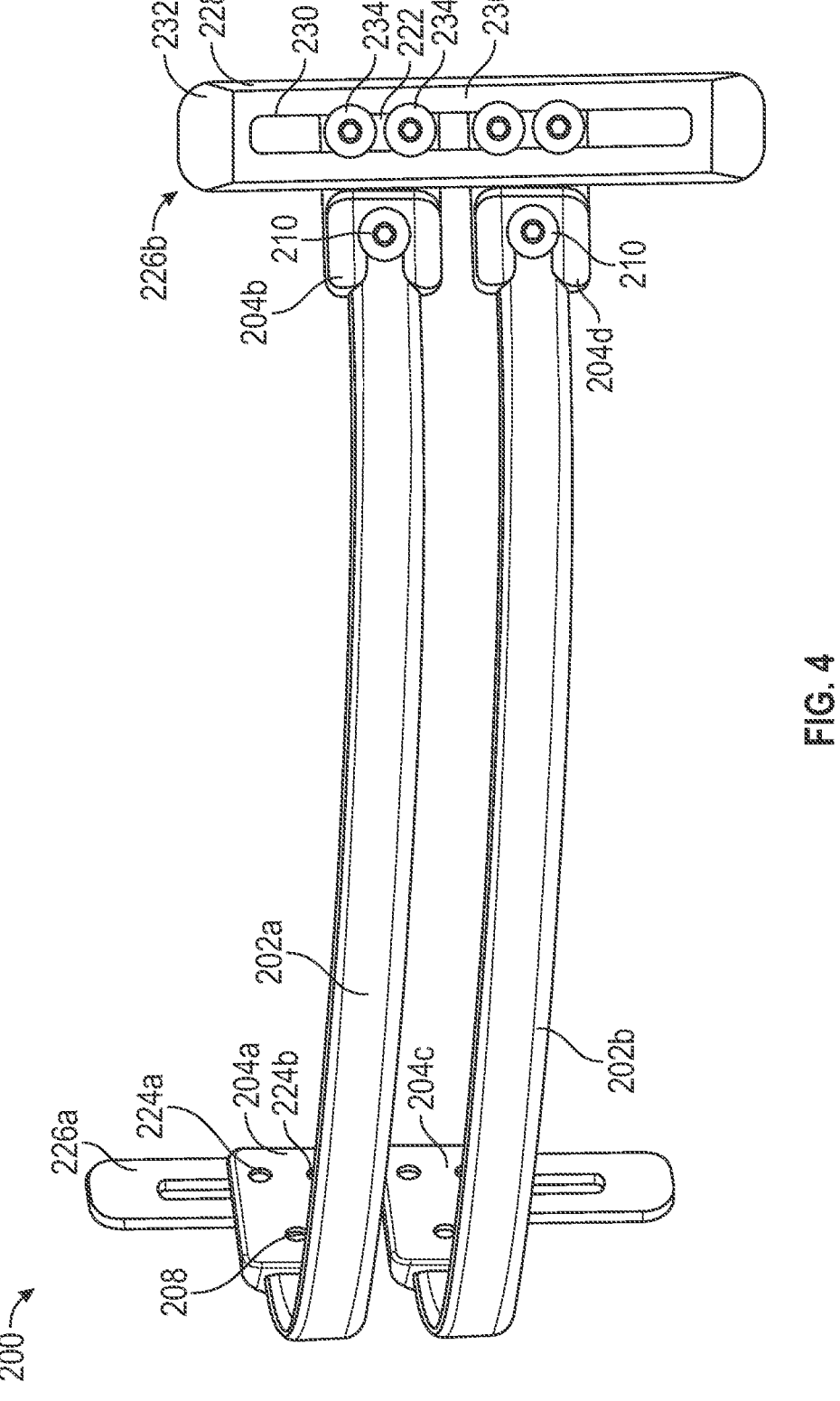
FIG. 4 illustrates an isometric view of a pectus bar assembly in a first configuration.
Figure 5:
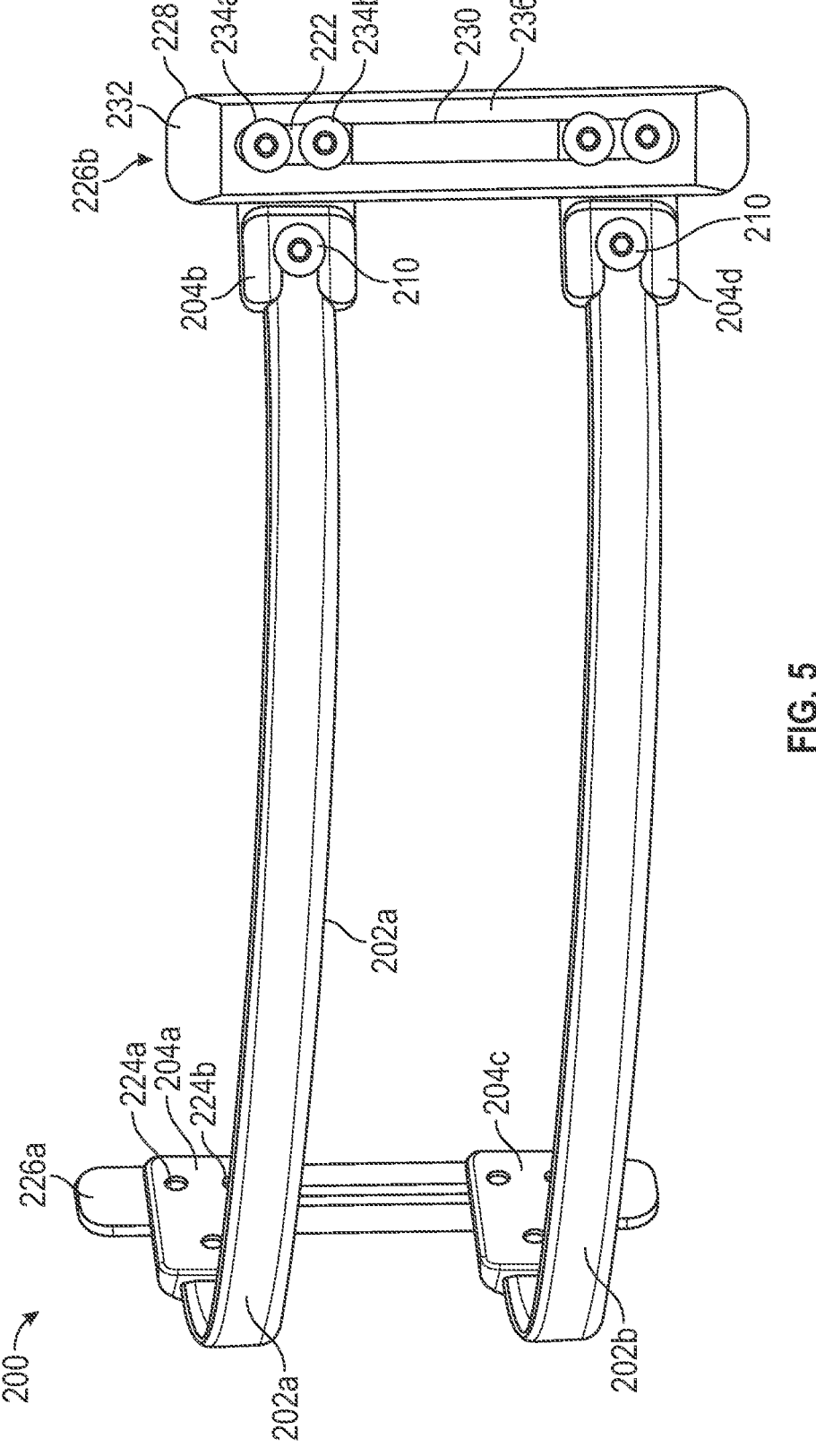
FIG. 5 illustrates an isometric view of a pectus bar assembly in a second configuration.

FIG. 4 illustrates an isometric view of the pectus bar assembly 200 in a first spacing configuration. FIG. 5 illustrates an isometric view of the pectus bar 200 assembly in a second spacing configuration. FIGS. 4 and 5 are discussed together below. The pectus bar assembly 200 of FIGS. 4-5 can be consistent with the pectus bar assembly 200 of FIGS. 2-3A discussed above. FIGS. 4-5 shows additional details of the stabilizers 204. Also, FIG. 4 shows the pectus bar assembly 200 adjusted to a spacing between the pectus bar 202a and the pectus bar 202b where one rib (e.g., one of the ribs 52) can be between the pectus bar 202a and the pectus bar 202b and FIG. 5 shows the pectus bar assembly 200 adjusted to a spacing between the pectus bar 202a and the pectus bar 202b where two ribs can be between the pectus bar 202a and the pectus bar 202b. FIGS. 4-5 also show additional components of the pectus bar assembly 200.

For example, FIGS. 4 and 5 show that the pectus bar assembly 200 can include a bridge 226a and a bridge 226b (collectively referred to as bridges 226). Each of the bridges 226 can include a body 228 defining a slot 230. The body 228 can include end portions 232 that can be tapered (or beveled or rounded), such as to help reduce palpability of the bridges following installation thereof. Each of the bridges 226 can be a rigid or semi-rigid component constructed of materials such as metals and plastics. For example, the bridges 226 can be constructed of biocompatible such as one or more of stainless steel alloys, cobalt-chromium, titanium, titanium alloys, polyether ether ketone (PEEK), polyether ketone ketone (PEKK), or the like.

The bridge 226b can be connectable to the stabilizers 204b and 204d to allow the stabilizer 204b and the first pectus bar 202a to translate along the bridge, and to allow the stabilizer 204d and the second pectus bar 202b to translate, independently of the first pectus bar 202a, along the bridge 226b. The bridge 226a can operate similarly to allow for independent adjustment or translation of the pectus bar 202a and the pectus bar 202b. The translation provided by the stabilizers of the pectus bars 202 is not limited or discrete. This can allow a surgeon to place the bars as desired or required by a procedure, whereas, many devices in the prior art includes holes at discrete increments to space apart pectus bars, which can limit options for placement in the pectus bars and result in interference with ribs.

The pectus bar assembly 200 can also include fasteners 234a and 234b (collectively referred to as fasteners 226). Each of the stabilizers 204 can receive fasteners 234a and 234b into bores 224a and 224b, respectively. The fasteners 234a and 234b can engage an outer surface 236 of the bridge 226b to secure the bridge 226b to the stabilizers 204b. The stabilizer 204d can be similarly connected to the bridge 226b and the stabilizers 204a and 204c can be similarly connected to the bridge 226a.

The slot 230 can be configured to receive at least a portion of the fasteners 234 therethrough to secure the stabilizer 204b to the bridge 226b. The slot 230 can also be configured to receive at least a portion of the boss 222 therein such that the boss 222 can be translatable within the slot 230 to enable translation of the stabilizer 204b along the bridge 226b. The boss 222 can be translatable within the slot 230 when the fasteners 234 are secured to the stabilizers 204b but not tightened against the outer surface 236 (or when the fasteners 234 are not secured to the stabilizers 204b), allowing for adjustment of the bars 202 during a procedure or allowing for connection of the stabilizers 204 to the bridges 226 at various locations.

For example, as shown in FIG. 4, the pectus bar 202a and the pectus bar 202b can be spaced apart from each other such that one rib can be located in between the bars 202a and 202b. However, as shown in FIG. 5, the stabilizers 204 can be connected to the bridges 226 such that two or more ribs can fit between the bars 202a and 202b. The stabilizers 204 can be translated between positions shown in FIGS. 4 and 5 when the stabilizers 204 are connected via the fasteners 234 and not tightened, as discussed above. When the fasteners 234a and 234b are secured to the bores 224a and 224b, respectively, and are tightened to engage the outer surface 236, movement of the stabilizers 204b with respect to the bridge 226b can be limited. Also, engagement by the boss 222 with ends of the slot 230 can limit translation of the stabilizers 204b with respect to the bridge 226b.

Figure 6:
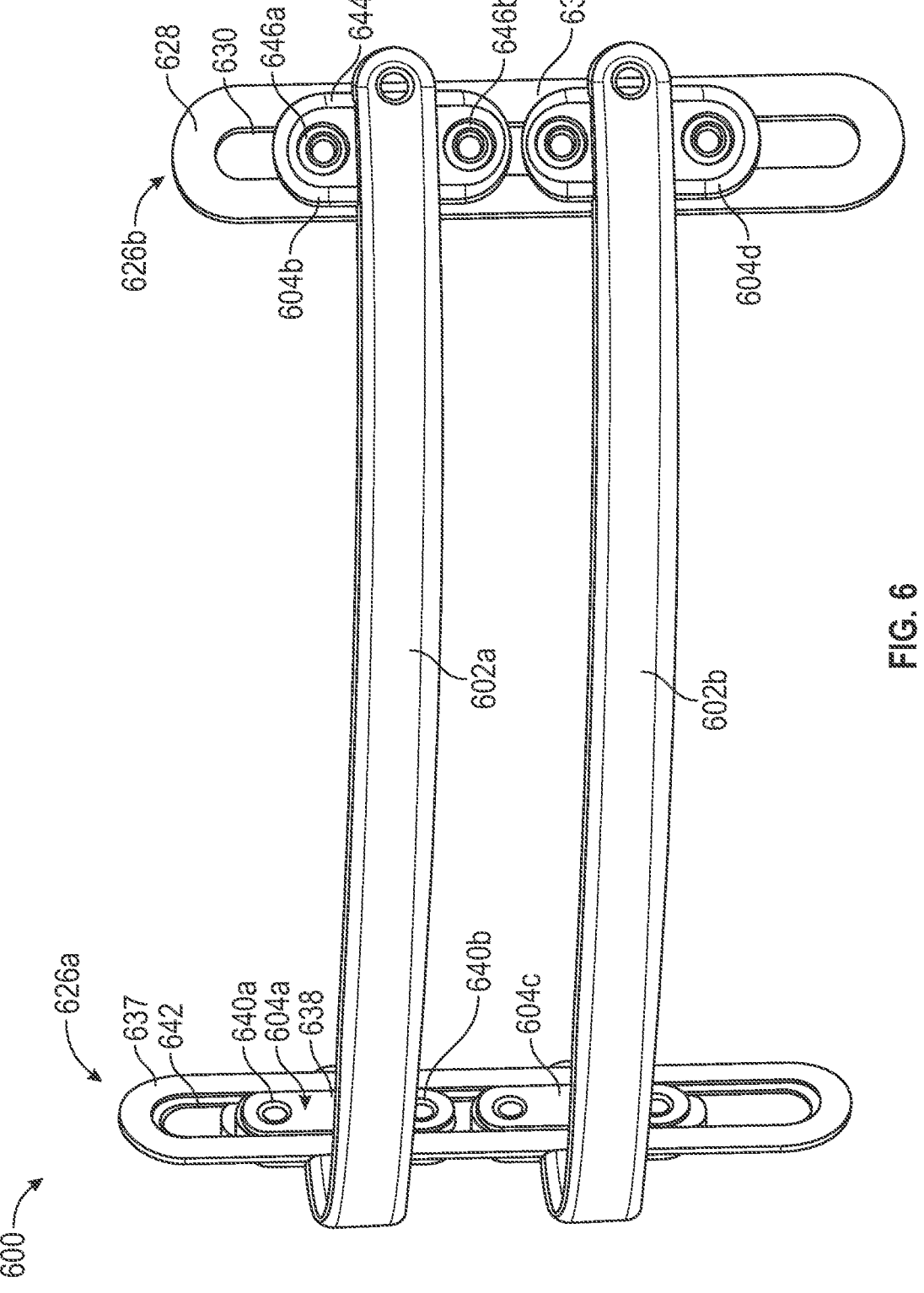
FIG. 6 illustrates an isometric view of a portion of a pectus bar assembly.
Figure 7:
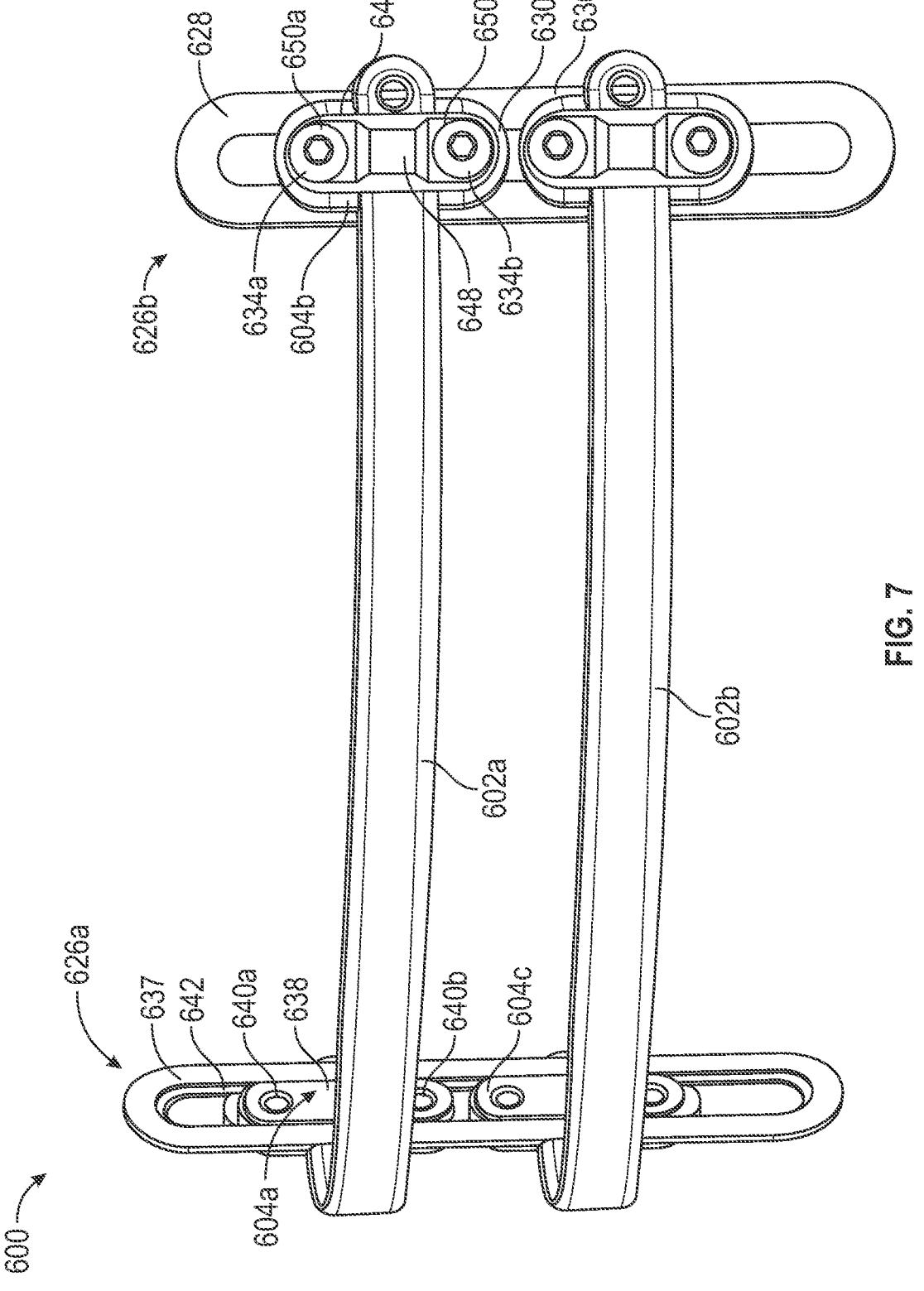
FIG. 7 illustrates an isometric view of a pectus bar assembly in a first configuration.
Figure 8:
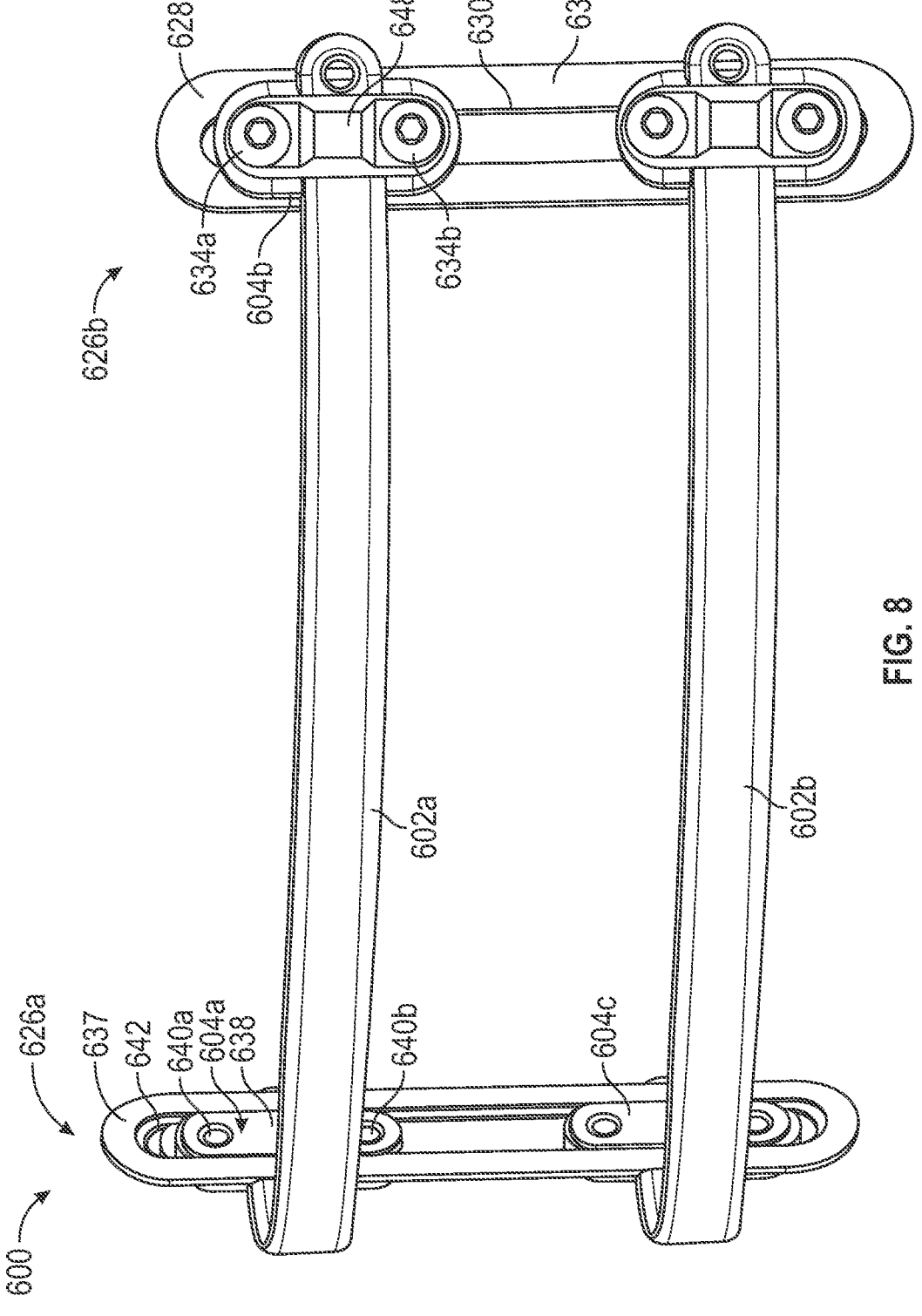
FIG. 8 illustrates an isometric view of a pectus bar assembly in a second configuration.

FIG. 6 illustrates an isometric view of a portion of a pectus bar assembly 600. FIG. 7 illustrates an isometric view of the pectus bar assembly 600 in a first configuration. FIG. 8 illustrates an isometric view of the pectus bar assembly 600 in a second configuration. FIGS. 6-8 are discussed together below. The pectus bar assembly 600 can be similar to the pectus bar assemblies discussed above. The pectus bar assembly 600 can include hardware for adjusting the bars vertically or the bridges horizontally. Any of the pectus bar assemblies discussed above or below can be modified to include the features of the pectus bar assembly 600.

The pectus bar assembly 600 can include pectus bars 602a and 602b, which can be similar to the bars 202a and 202b, discussed above. The pectus bar assembly 600 can also include stabilizers 604a-604d. The stabilizers 604a and 604b can be configured to connect to the pectus bar 602a and the stabilizers 604C and 604D can be configured to connect to the pectus bar 602b.

Each of the stabilizers 604 can include a base 638, as shown most clearly in FIG. 6. Each base 638 can include bores 640a and 640b that can be configured to receive fasteners 634a and 634b, respectively, at least partially therein, as shown in FIGS. 7-8. For example, the bores 640a and 640b can be threaded to receive screws or bolts. The base 638 can be configured to engage a first side (or back side or posterior side) 637 of the bridge 626. The base can also be insertable into a recess 642 of the bridge 626, which can at least partially surround a slot 630 of the bridge 626.

Each of the stabilizers 604 can also include a plate 644, as shown most clearly in FIG. 6. The plate 644 can engage a second side 636 (or front side or anterior side) of the bridge 626 and can connect to the plate 644, such as through a snap interface. A portion of the base 638 or a portion of the plate 644 can extend at least partially through the slot 630 to secure the base 638 and the plate 644 to the bridge 626. When the base 638 and the plate 644 are connected to the bridge 626, the base 638 and the plate 644 can be translatable along the slot 630. The plate 644 can also include bores 646a and 646b that can be aligned with the bores 640a and 640b of the base 638 when the base 638 is connected to the plate 644. As shown in FIG. 6, the plate 644 can engage a first side of the pectus bar 602a.

As shown in FIGS. 7 and 8, each of the stabilizers 604 can include a cap 648. The cap 648 can be engageable with the pectus bar 602a and can be securable to the plate 644. The cap 648 can include bores 650a and 650b configured to receive fasteners 634a and 634b at least partially therein or therethrough. For example, at least a portion of the fasteners 634a and 634b can extend through bores 650a and 650b of the cap 648, respectively, and through bores 646a and 646b of the plate 644, respectively, and into the bores 640a and 640b of the base 638, respectively, to secure the cap 648, the plate 644, and the base 638 to each other.

When the fasteners 634a and 634b are secured to the cap 648, the plate 644, and the base 638, but not tightened, the cap 648, the plate 644, the base 638, and the pectus bar 602a can be translatable along the bridge 626b. For example, as shown in FIG. 7, the pectus bar 602a and the pectus bar 602b can be spaced apart from each other such that one rib can be located in between the bars 602a and 602b. As shown in FIG. 8, the stabilizers 604 can be translated along the bridges 626a and 626b such that two or more ribs can fit between the bars 602a and 602b. That is, the stabilizers 604 can be translated between the positions shown in FIGS. 7 and 8 when the cap 648, the base 638, and the plate 644 are connected and the fasteners 634 are not tightened.

Also, when the fasteners 634a and 634b are secured to the cap 648, the plate 644, and the base 638, but the fasteners 634a and 634b are not tightened, the cap 648, the plate 644, the base 638, and the bridge 626b can be translatable along the pectus bar 602a. And, the bridges 626 and stabilizers 604 can be translated along the bars 602 when the fasteners 634 are connected to the cap 648 and the base 638 but are not tightened. When the fasteners 634a and 634b are tightened to the cap 648, the plate 644, and the base 638, translation of the stabilizers 604 (and the bars 602) with respect to the bridges 626 can be limited or prevented and translation of the stabilizers 204 and the bridges 626 with respect to the bars 602 can be limited or prevented. In this way, the assembly 600 can allow for intraoperative adjustment of the hardware as necessary to fit an individual patient.

Figure 9:
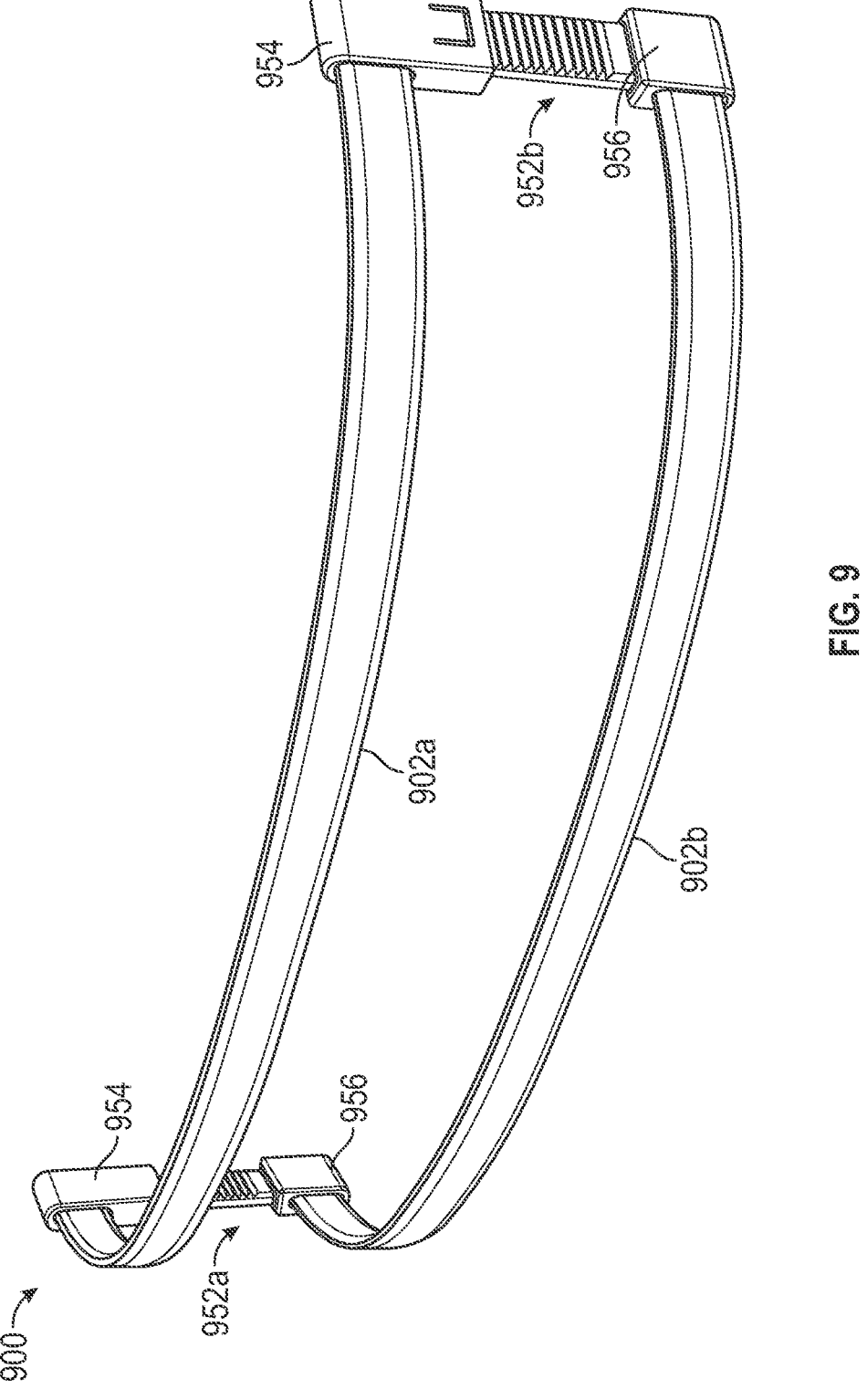
FIG. 9 illustrates an isometric view of a pectus bar assembly.

FIG. 9 illustrates an isometric view of a pectus bar assembly 900. The pectus bar assembly 900 can be similar to the pectus bar assemblies discussed above. The pectus bar assembly 900 can include hardware for quickly securing the pectus bars to each other. Any of the pectus bar assemblies discussed above or below can be modified to include the features of the pectus bar assembly 900.

The pectus bar assembly 900 can include a pectus bar 902a and a pectus bar 902b, which can be similar to the pectus bars discussed above. The pectus bar assembly 900 can also include a stabilizer assembly 952a and a stabilizer assembly 952b. Each of the stabilizer assemblies can include a first bracket 954 and a second bracket 956. The first brackets 954 can be connected to the pectus bar 902a and the second brackets 956 can be connected to the pectus bar 902b. Optionally, one of the first brackets 954 and one of the second brackets 956 can be connected to the pectus bar 902a and one of the first brackets 954 and one of the second brackets 956 can be connected to the pectus bar 902b. That is one of the stabilizer assemblies 952 can be connected to the bars 902 in a configuration opposite the other.

Each of the first brackets 954 and the second brackets 956 can be a rigid or semi-rigid components constructed of materials such as metals and plastics. For example, the first brackets 954 and the second brackets 956 can be constructed of biocompatible such as one or more of stainless steel alloys, cobalt-chromium, titanium, titanium alloys, polyether ether ketone (PEEK), polyether ketone ketone (PEKK), or the like.

Figure 10:
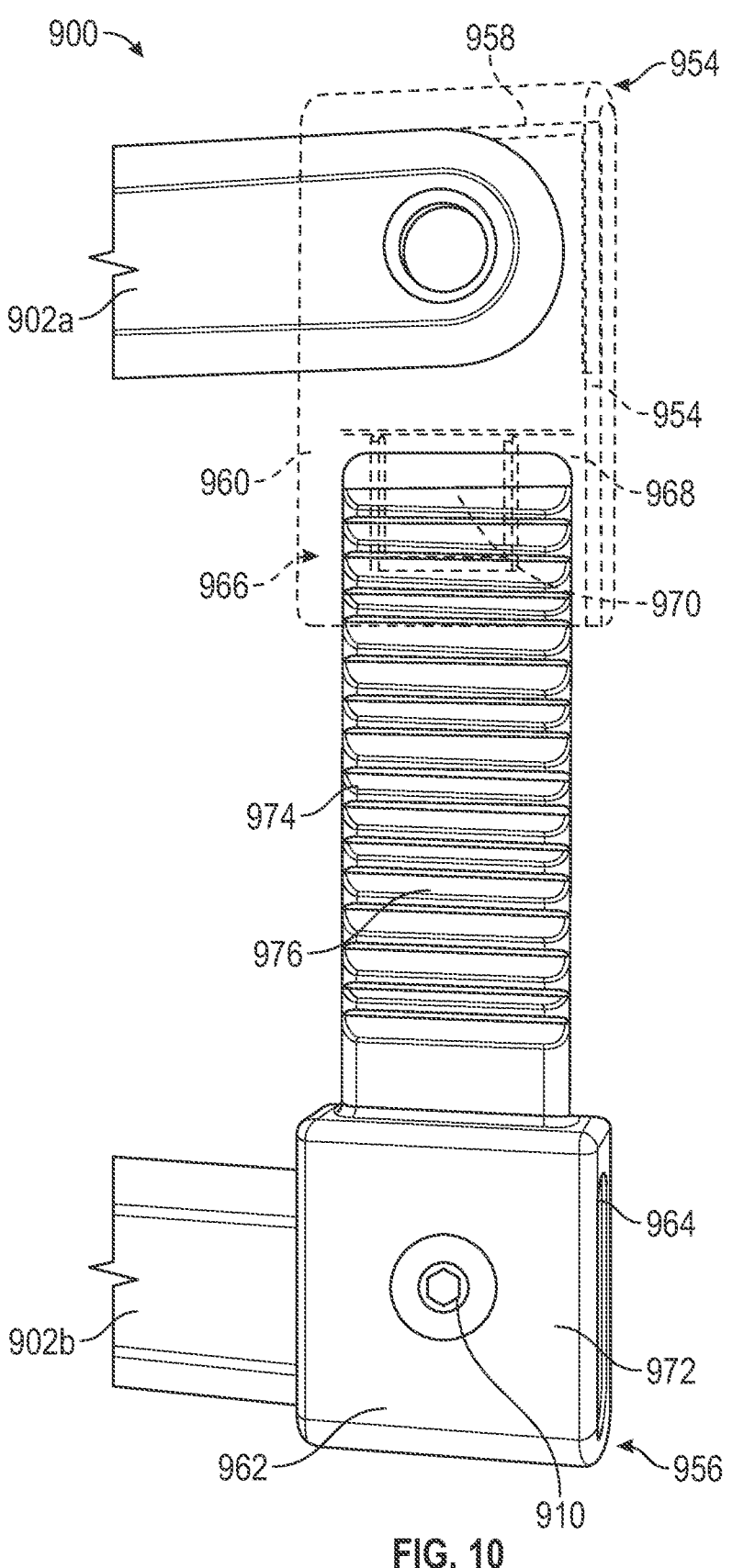
FIG. 10 illustrates an enlarged isometric view of a portion of a pectus bar assembly.

FIG. 10 illustrates an enlarged isometric view of a portion of the pectus bar assembly 900. The pectus bar assembly 900 of FIG. 10 can be consistent with the pectus bar assembly 900 of FIG. 9; FIG. 10 shows additional details of the pectus bar assembly 900. For example, FIG. 10 shows that the first bracket 954 can include a bar slot 958, which can be a recess, opening, or bore extending at least partially into a body 960 of the first bracket 954. The bar slot 958 can extend entirely through the body 960 such as to allow the pectus bar 902a to pass through the first bracket 954. Optionally, the bar slot 958 can extend only partially into the body 960, such as to limit movement of the pectus bar 902a with respect to the first bracket 954.

Similarly, the second brackets 956 can include a bar slot 964, which can be a recess, opening, or bore extending at least partially into a body 962 of the second bracket 956. The bar slot 964 can extend entirely through the body 962 such as to allow the pectus bar 902b to pass through the second bracket 956. Optionally, the bar slot 964 can extend only partially into the body 962, such as to limit movement of the pectus bar 902b with respect to the second bracket 956.

The first bracket 954 can also include a receiver 966 defining a slot 968 extending at least partially into the body 960. The slot 968 can terminate within the body 960 prior to interesting the bar slot 958. The slot 968 can be orthogonal to the bar slot 958 or can be in an orientation not parallel to the bar slot 958. The first bracket 954 can also include a pawl 970 connected to the receiver 966. The pawl 970 can include one or more projections extending at least partially into the slot 968. The pawl 970 can be configured to reversibly deflect. The pawl 970 can be integrally formed into the body 960, such as via a living hinge. Optionally, the pawl 970 can be connected to the body 960.

The second bracket 956 can include a projection 974 extending from a body 972 of the second bracket 956. The projection 974 can be insertable into the receiver 966 to connect the first bracket 954 to the second bracket 954 and to secure the first pectus bar 902a to the second pectus bar 902b. The projection 974 and the receiver 966 can together form a ratcheting interface to secure the first bracket 954 to the second bracket 956. For example, the projection 974 can include a plurality of teeth 976, which can be engageable with the pawl 970 when the projection 974 is inserted into the receiver 966. The pawl 970 can engage the teeth 976 and deflect when the projection 974 moves into the receiver and the pawl 970 can engage and retain one or more of the teeth 976 to limit movement of the projection 974 out of the receiver 966. In this way, the receiver 966 and the projection 974 can be relatively quickly and securely connected to secure the pectus bar 902a to the pectus bar 902b.

Also, optionally, the projection 974 can be engageable with the slot 968 to limit translation of the projection 974 into the slot. For example, the projection 974 can be measured and cut to a desired length prior to insertion such that engagement between the projection 974 and the slot 968 can be used to position the bars pectus bar 902a and pectus bar 902b with respect to each other.

Optionally, the pectus bar assembly 900 can include one or more fasteners, such as a fastener 910, which can be threadably securable to a bore of the second bracket 956 and can be insertable through a bore of the pectus bar 902b, such as to limit translation of the pectus bar 902b with respect to the second bracket 956. The first bracket 954 can optionally be similarly configured.

Figure 11:
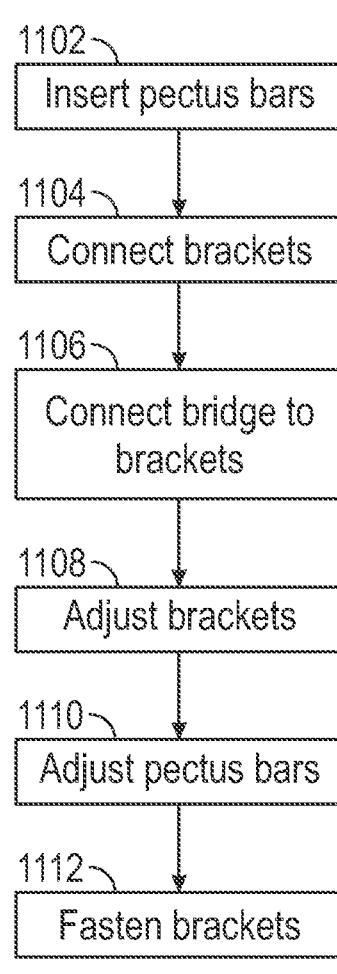
FIG. 11 illustrates a schematic view of a method.

FIG. 11 illustrates a schematic view of the method 1100, in accordance with at least one example of this disclosure. The method 1100 can be a method of installing a pectus bar. More specific examples of the method 1100 are discussed below. The steps or operations of the method 1100 are illustrated in a particular order for convenience and clarity; many of the discussed operations can be performed in a different sequence or in parallel without materially impacting other operations. The method 500 as discussed includes operations performed by multiple different actors, devices, and/or systems. It is understood that subsets of the operations discussed in the method 500 can be attributable to a single actor, device, or system could be considered a separate standalone process or method.

The method can begin at step 1102, which can be inserting a first pectus bar and a second pectus bar into a thoracic cavity, such as the pectus bar 202a and the pectus bar 202b. At step 1104, a first bracket can be connected to the first pectus bar and a second bracket can be connected to the second pectus bar. For example, the stabilizer 204b can be connected to the pectus bar 202a and the stabilizer 204d can be connected to the stabilizers 204b.

At step 1106, a bridge can be connected to the first bracket and the second bracket. For example, the bridge 226b can be connected to the stabilizers 204b and 204d. At step 1108, the first and second bracket can be adjusted with respect to the bridge. For example, the stabilizers 204b or 204d can be translated along the bridge 226b. At step 1110, the pectus bars can be adjusted with respect to the bridges. For example, the pectus bar 602a and the pectus bar 602b can be adjusted with respect to the stabilizers 604a-604d by translating the stabilizers (and the bridges 626) along the pectus bars 602. At step 1114, the brackets can be fastened. For example, the stabilizers 204 can be fastened or otherwise secured to the bridges 226, such as to secure the pectus bars 202 to the bridges 226. Additional steps discussed above with respect to FIGS. 2-10 can be incorporated into the method 1100.

Figure 12:
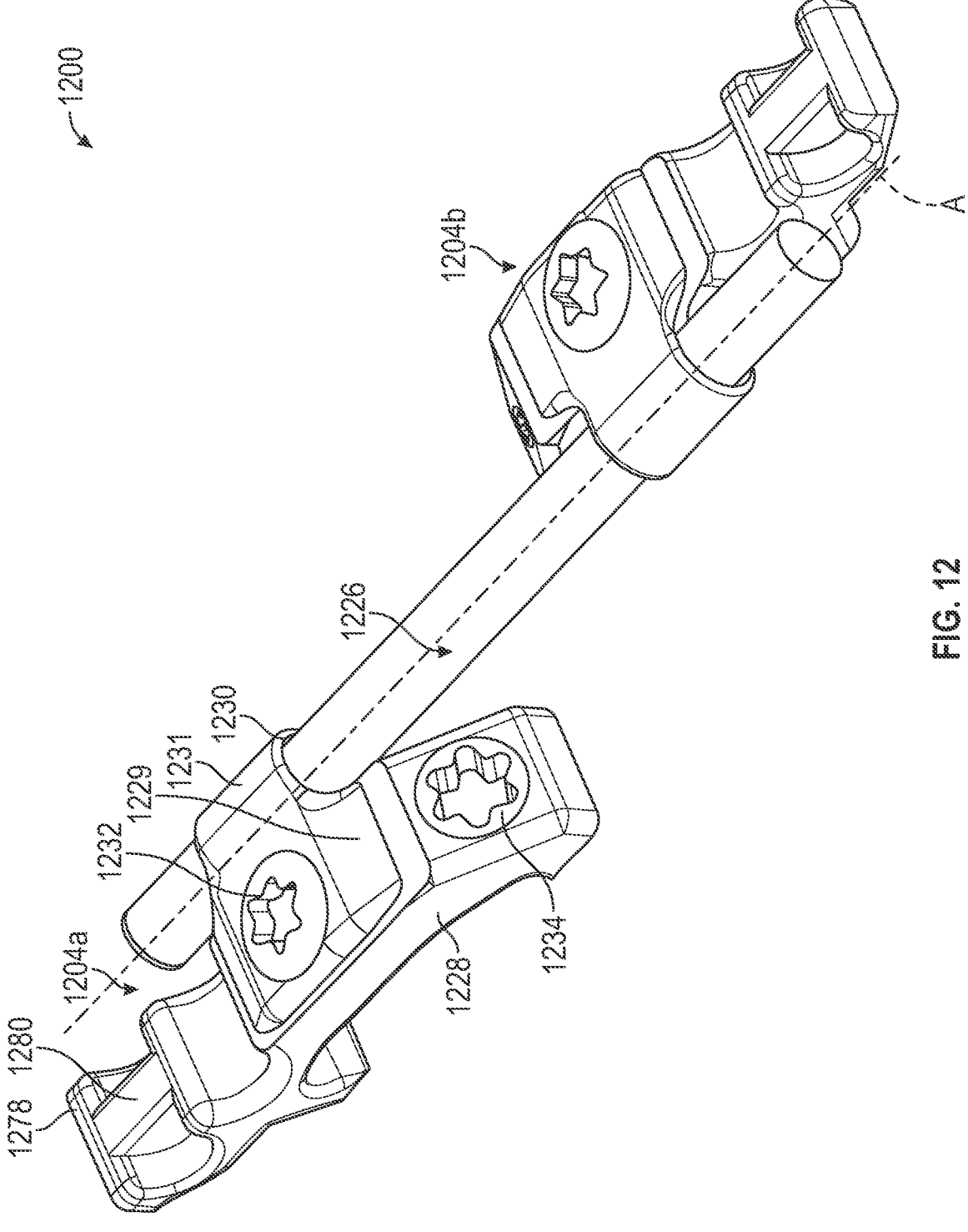
FIG. 12 illustrates an isometric view of a portion of a pectus bar assembly.

FIG. 12 illustrates an isometric view of a portion of a pectus bar assembly 1200. The pectus bar assembly 1200 can be similar to the pectus bar assemblies discussed above or below. The pectus bar assembly 1200 can include bar links securable to pectus bars and securable to a bridge to help stabilize the assembly following implantation.

The pectus bar assembly 1200 can include a first pectus bar 1202a and a second pectus bar 1202b (both shown in FIG. 18) and a first bar link 1204a and a second bar link 1204b. The pectus bar assembly 1200 can also include a bridge 1226. Though the pectus bar assembly 1200 is discussed as including two pectus bars and two bar links, the pectus bar assembly 1200 can include 1, 2, 3, 4, 5, 6, or the like pectus bars, and can include 1, 2, 3, 4, 5, 6, or the like bar links (or stabilizers or brackets).

The pectus bars 1202 can be similar to the pectus bars discussed above (e.g., the 202) in that the pectus bars 1202 can be a rigid or semi-rigid bar constructed of one or more biocompatible materials such as metals and plastics. For example, the pectus bars 1202 can be constructed of biocompatible materials such as one or more of stainless-steel alloys, cobalt-chromium, titanium, titanium alloys, polyether ether ketone (PEEK), polyether ketone ketone (PEKK), or the like. The pectus bars 1202 can have an elongate body forming a curve, such as a c-shape, and can be rigid (or semi-rigid) but flexible enough to be bent to match a curvature of a patient's ribcage using tools, such as a bar bender.

The bar links 1204a and 1204b can each be connectable to portions of the pectus bars 1202a and 1202b, respectively, and the bar links 1204a and 1204b can be translatable along the pectus bars 1202a and 1202b, respectively, as discussed in further detail below. Each of the bar links 1204a and 1204b can be a rigid or semi-rigid component constructed of materials such as metals and plastics. For example, the bar links 1204a and 1204b can be constructed of biocompatible such as one or more of stainless-steel alloys, cobalt-chromium, titanium, titanium alloys, polyether ether ketone (PEEK), polyether ketone ketone (PEKK), or the like. The bar links 1204a and 1204b can be the same configuration but rotated; in other examples the bar links 1204a and 1204b can be mirror copies of each other.

The bridges 1226 can be connected to the pectus bars 1202 by the bar links 1204 such as to reinforce the pectus bars 1202 as an assembly. Each of the bridges 226 can be a rigid or semi-rigid component constructed of materials such as metals and plastics. For example, the bridges 226 can be constructed of biocompatible such as one or more of stainless steel alloys, cobalt-chromium, titanium, titanium alloys, polyether ether ketone (PEEK), polyether ketone ketone (PEKK), or the like. The bridges can be cylindrical in shape but can have other shapes such as a rectangular prism, hexagonal prism, octagonal prism, or the like.

Each of the bar links 1204 can include a body 1228 and an arm 1229 connected to the body 1228. The body 1228 and the arm 1229 can together form a slot 1230 to receive the bridge 1226 at least partially therein or therethrough. The arm 1229 can be connected to the body 1228 by a living hinge 1231 and the arm 1229 and the body 1228 can together form a clamp biased to an open position by the living hinge 1231. The living hinge 1231 can be integral to the body 1228 and the arm 1229, and the living hinge 1231 can at least partially form the slot 1230. The living hinge 1231 can be configured to elastically deform, flex, or move to enable relative movement of the arm 1229 with respect to the body 1228 which can cause a change in size of the slot 1230.

Figure 13:
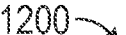
FIG. 13 illustrates an isometric view of a portion of a pectus bar assembly.

The bar links 1204 can also include an arm actuator 1232 that can be connected to the body 1228 and to the arm 1229. The arm actuator 1232 can extend through the arm 1229 and can threadably engage a bore 1240 (shown in FIG. 13) of the body 1228, where the bore 1240 can be threaded. The arm actuator 1232 can be a set screw, cam, screw, bolt, fastener or the like that can be operable to move between a first position where the bridge 1226 is movable with respect to the body 1228 and a second position where the arm 1229 and the body 1228 engage the bridge 1226 to clamp the bridge 1226 to secure the bar links 1204 to the bridge 1226. Because the arm 1229 is connected to the body 1228 by the living hinge 1231, when the arm actuator 1232 causes the arm 1229 to move, the living hinge 1231 can allow the arm 1229 to elastically deflect with respect to the body 1228. The arm 1229 can also be biased by the living hinge 1231 to an open or partially open position. Each of the bar links 1204 can also include an actuator 1234 that can be connected to the body 1228 and can be operable to secure the bar links 1204 to pectus bars, as discussed in further detail below.

When the arm 1229 (e.g., of the bar link 1204a) is in the open or unlocked position, the bar link 1204a can be translatable or movable along an axis A of the bridge 1226. The bar link 1204a can also be rotatable about the bridge 1226 (e.g., about the axis A of the bridge 1226). The bar links 1204 be independently adjustable along the bridge

1226 and around the bridge 1226. Optionally, if the bar links 1204 are fixed to the pectus bars, the bridge 1226 can be adjusted relative to the bar links 1204. The translation and rotation provided by the bar links 1204 is not limited or discrete. This can allow a surgeon to place the bars as desired or required by a procedure, whereas many devices in the prior art include holes at discrete increments to space apart pectus bars, which can limit options for placement in the pectus bars and can result in interference with ribs.

FIG. 12 also shows that the bar links 1204 can each include a head 1278 that can be connected to the body 1228. The head 1278 can be used by a physician to position the bar links 1204 with respect to anatomy, the pectus bars 1202, or the bridge 1226. The head 1278 can also include a rib 1280 that can be configured to be grasped by an instrument, such as a needle holder or forceps, to maneuver or position the bar links 1204, which can be helpful for positioning with respect to the bridge 1226 when the bridge 1226 is a cylindrical rod, as shown in FIG. 12. The head 1278 can also be used to at least partially deform the body 1228 for extraction or explantation of one or more components of the pectus bar assembly 1200, as discussed in further detail below. The head 1278 can be lower than (e.g., posterior of) the arm 1229 to help limit or reduce palpability of the head 1278.

Figures 14, 15, 16, 17:
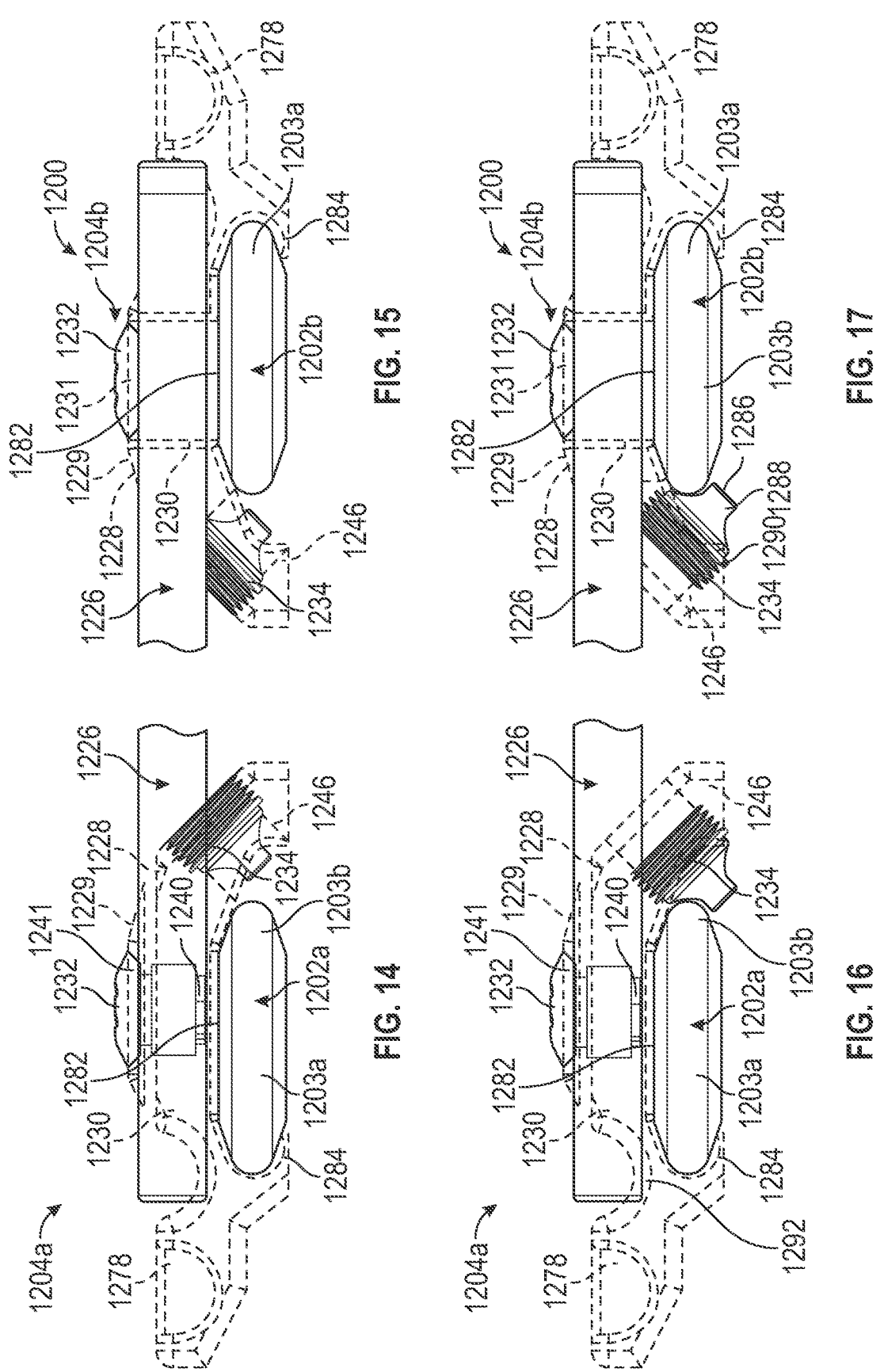
FIG. 14 illustrates a side view of a portion of a pectus bar assembly.
FIG. 15 illustrates a side view of a portion of a pectus bar assembly.
FIG. 16 illustrates a side view of a portion of a pectus bar assembly.
FIG. 17 illustrates a side view of a portion of a pectus bar assembly.

FIG. 14 illustrates a side view of a portion of the pectus bar assembly 1200. FIG. 15 illustrates a side view of a portion of the pectus bar assembly 1200. FIG. 16 illustrates a side view of a portion of the pectus bar assembly 1200. FIG. 17 illustrates a side view of a portion of the pectus bar assembly 1200. FIGS. 14-17 are discussed together below. The pectus bar assembly 1200 of FIGS. 14-17 can be consistent with FIGS. 12 and 13 above; FIGS. 14-17 show additional details of the pectus bar assembly 1200. For example, FIGS. 14-17 show the pectus bars 1202a and 1202b and how the bar links 1204a and 1204b can connect to the first pectus bars 1202a and 1202b, respectively.

FIGS. 14-17 also show additional details of the bar links 1204. For example, FIGS. 14-17 show that each of the bodies 1228 of the bar links 1204 can include or can define an opening 1282 that can be configured to receive at least a portion of the pectus bar 1202 therein. The opening 1282 can be at least partially defined by a shelf 1284 of the body. The shelf 1284 can be shaped to conform to either end portion 1203a or 1203b of the first pectus bar 1202a or the second pectus bar 1202b. That is, the shelf 1284 can receive, for example, the end portion 1203a at least partially therein when the first pectus bar 1202a is inserted into the opening 1282, as shown in FIGS. 14-17. The shelf 1284 and the actuator 1234 can be together shaped and sized to allow the bar links 1204 to be placed onto the pectus bars 1202 from above (or anteriorly).

FIGS. 14-17 shows further details of the bore 1240 of the arm actuator 1232, which can extend at least partially through the body 1228. Also, the arm 1229 can include an actuator bore 1241 that can extend at least partially through the arm 1229 and can be aligned (e.g., coaxial with) the bore 1240. An upper portion of the actuator bore 1241 can be tapered or otherwise angled to be complementary to an underside of a head of the arm actuator 1232 such that the arm actuator 1232 cannot pass through the arm 1229 towards the body 1228. The body 1228 can include a swage of the bore 1240 in the body 1228 that can be configured, together with the head and the actuator bore 1241, to help captivate or capture the arm actuator 1232. Optionally, the bore 1240 can be threaded to engage with a threaded portion of the arm actuator 1232 such that when the arm actuator 1232 is rotated (e.g., clockwise), the arm actuator 1232 moves into the body 1228, bringing the arm 1229 closer to the body 1228, closing the slot 1230 and clamping down onto the bridge 1226 to limit rotation of the bar link 1204*a* with respect to the bridge 1226 and limiting translation of the bar link 1204*a* along the bridge 1226. The bar link 1204*b* can be similarly configured or operated.

FIGS. 14-17 also show an actuator 1234 located at least partially within a bore 1246 of the body 1228 of each of the bar links 1204. The actuator 1234 can be a set screw, cam, screw, bolt, fastener or the like that can be operable to move between a first position (shown in FIGS. 14 and 15) where the pectus bar(s) 1202 are movable with respect to the body 1228 and between a second position where the actuator 1234 engage the pectus bar(s) 1202 to clamp the bar links 1204 to the pectus bar(s) 1202. As shown in FIGS. 14 and 15, the actuator 1234 can be in a fully retracted position, which can allow, for example, the pectus bar 1202*a* to be inserted into the opening 1282 of the bar link 1204*a*. The actuator 1234 can be translated relative to the body 1228 by rotating the actuator 1234 with respect to the body 1228, such as with a cam, screw, or bolt.

The actuator 1234 can be limited or prevented from moving beyond the retracted position by a stop, swage, or the like of the actuator 1234, which can be configured to help capture or captivate the actuator 1234 at least partially within the bore 1246. During assembly, the actuator 1234 can be threaded into the bore 1246 from the opening 1282. Following insertion, the actuator 1234 can be swaged near its proximal side (or anterior side, such as away from the opening 1282). Similarly, the actuator 1234 can be limited or prevented from moving beyond the extended position by a stop, such as a thread run-out at a distal portion of the actuator 1234 or other stop of the bore 1246 or the actuator 1234.

As shown in FIGS. 16 and 17, the actuators 1234 can be operated (e.g., rotated through a threaded portion of the bore 1246) to engage a second end portion 1203*b* of the pectus bars 1202 to cause the first end portion 1203*a* to engage the shelf 1284 opposite the actuator 1234, thereby securing the bar links 1204 to the pectus bars 1202. Such engagement can be reversed by reversing (e.g., rotating in a counter-clockwise direction) the actuator 1234 to release the bar links 1204 from the pectus bars 1202.

As shown in FIG. 17, the actuator 1234 can be shaped such that it has a flat distal tip 1286 connected to a curved, arced, or radiused portion 1288 that is connected to a body 1290, which can be a threaded portion (e.g., threaded portion 1290). The radiused portion 1288 can be configured to engage a curved surface or portion of the second end portion 1203*b*. The arc or radius of curvature of the radiused portion 1288 can be complementary (e.g., shaped to receive or conform to) the end portion 1203*b*. The radius of curvature of the radiused portion 1288 can be between 0.5 millimeters (mm) and 2.5 mm, such as between 1 mm and 2 mm. For example, the radius of curvature can be 1.1 mm, 1.2 mm, 1.3 mm, 1.4 mm, 1.5 mm, 1.6 mm, 1.7 mm, 1.8 mm, 1.9 mm, or the like. Also, the distal tip 1286 can have a diameter of between 0.5 mm and 2.5 mm, such as between 1 mm and 2 mm. For example, the diameter of the distal tip 1286 can be 1.1 mm, 1.2 mm, 1.3 mm, 1.4 mm, 1.5 mm, 1.6 mm, 1.7 mm, 1.8 mm, 1.9 mm, or the like. In one example, the distal tip can be about 1.6 mm and the radius of curvature can be about 1.65 mm.

The flat distal tip 1286 and the radiused portion 1288 can also together be shaped such that the flat distal tip 1286 does not engage the end portion 1203*b* as the actuator 1234 extends from its retracted position to the extended position when the pectus bar 1202*a* is in the opening 1282, which could result in a force applied to the pectus bar 1202*b* that forces the pectus bar 1202*b* out of the opening 1282. Instead, the flat distal tip 1286 and the radiused portion 1288 can be shaped such that as the actuator 1234 extends into the opening 1282, the flat distal tip 1286 does not engage the second pectus bar 1202*b* and only the radiused portion 1288 engages the end portion 1203*b* to apply a force towards the body 1228 or the shelf 1284, helping to simplify installation of the pectus bar assembly 1200.

FIGS. 14-17 also show that the head 1278 can extend from the body 1228 away from the actuator 1234 and the head 1278 can be connected to a body 1228 on the same side as the shelf 1284. The body 1228 can also include a recess 1292 (shown in FIG. 16) that can create a relatively thin portion of the body 1228 between the recess 1292 and the shelf 1284, which can be used as discussed in FIG. 18 below.

Figure 18:
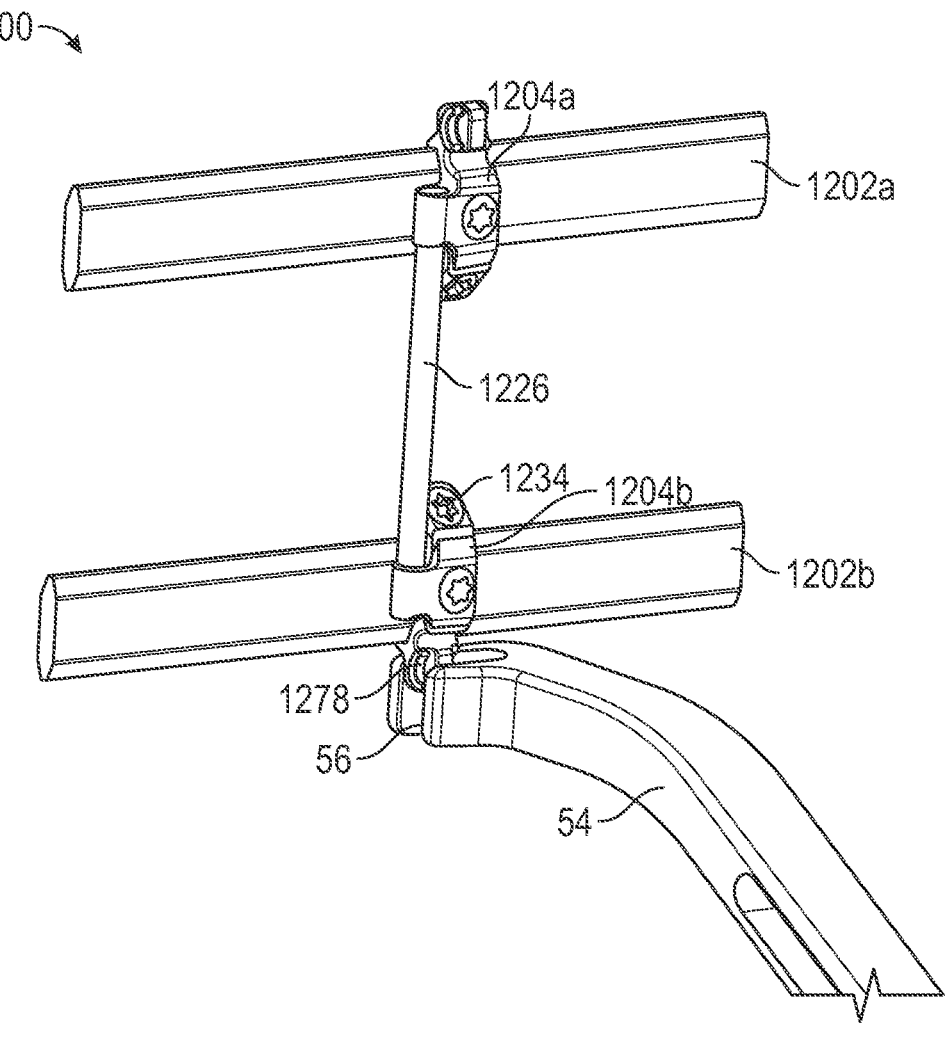
FIG. 18 illustrates an isometric view of a pectus bar assembly.

FIG. 18 illustrates an isometric view of the pectus bar assembly 1200. The pectus bar assembly 1200 of FIG. 18 can be consistent with FIGS. 12-17 discussed above. FIG. 18 shows how the head 1278 can be used. For example, during an extraction, removal or explantation of one or more components of the pectus bar assembly 1200, it may be required to remove the bar link 1204*b* from the second pectus bar 1202*b*, which can require that the actuator 1234 be actuated to disengage the second pectus bar 1202*b*. However, tissue or bone can grow over or into the recess of the actuator 1234 that is configured to receive a tool or instrument, such as a hexolubular interface, hexagonal interface, cross-recess interface, or the like. In such a situation, it may be difficult to insert the instrument into the interface or can be time consuming to clear debris. When this occurs, the head 1278 can be inserted into an opening 56 of a bender 54 and the bender 54 can be operated to deform the body 1228 such that the body 1228 bends about the recess 1292 (shown in FIG. 16) and the opening 1282 increases in size to allow the bar links 1204*b* to be removed from the second pectus bar 1202*b* without operating the actuator 1234. The head 1278 of the bar links 1204*a* can be similarly manipulated to free the bar links 1204*a* from the first pectus bar 1202*a* allowing for explantation of the pectus bar assembly 1200 without actuation of the actuator 1234.

Figure 19:
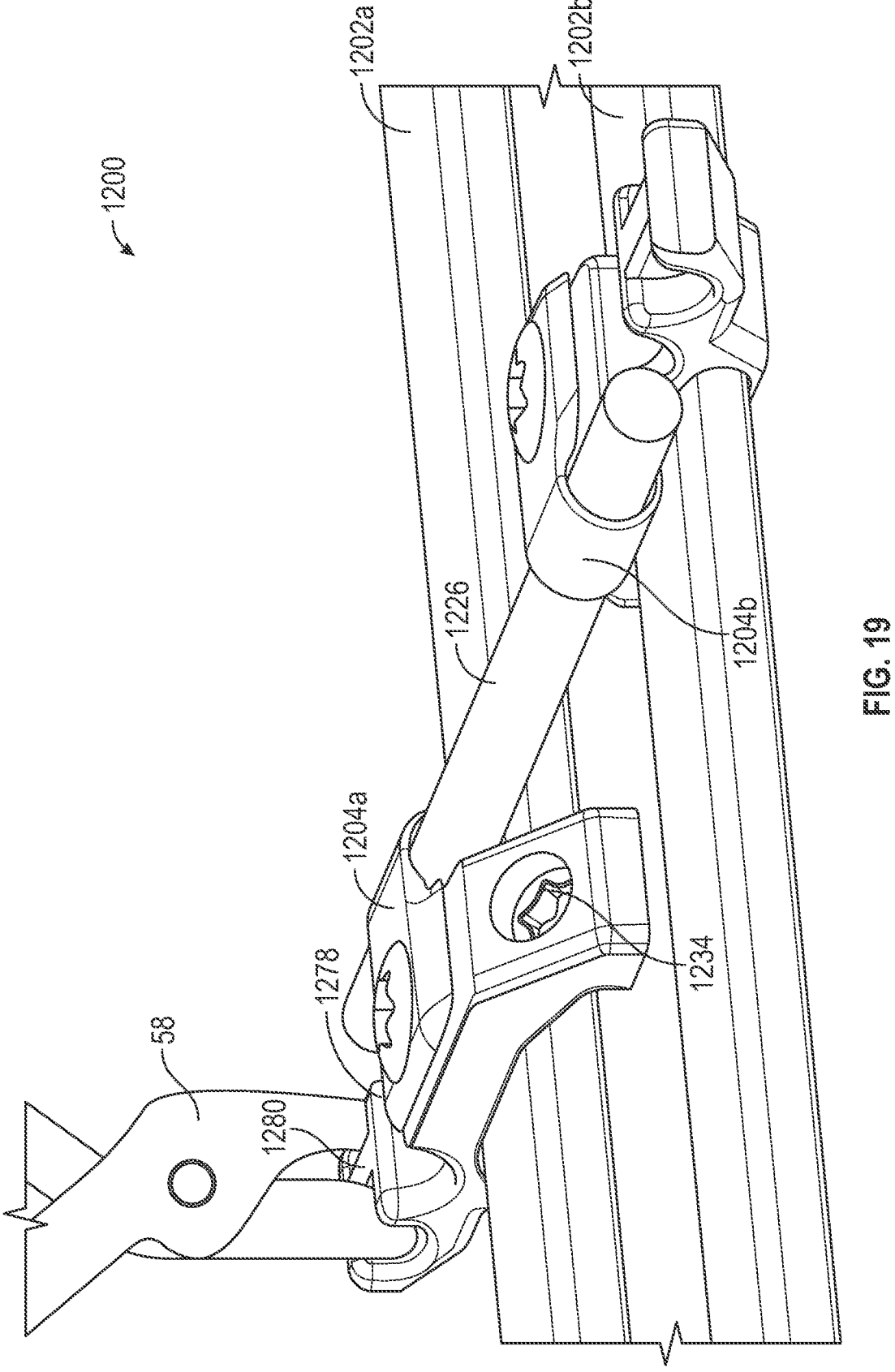
FIG. 19 illustrates an isometric view of a portion of a pectus bar assembly.

FIG. 19 illustrates an isometric view of a portion of the pectus bar assembly 1200. The pectus bar assembly 1200 of FIG. 19 can be consistent with FIGS. 12-18 discussed above. FIG. 19 shows other ways that the head 1278 can be used. For example, during installation or during extraction, it may be desired to manipulate or position the bar link 1204*a* with respect to the first pectus bar 1202*a*, the bridge 1226, or anatomy. In such a case, a grasping instrument 58 (e.g., an instrument including jaws, such as a needle holder or forceps) can be used to grasp the rib 1280 allowing a physician or surgeon to position the bar links 1204*a* easily using the instrument 58, such as along the bridge 1226 or around the bridge 1226.

Figure 20:
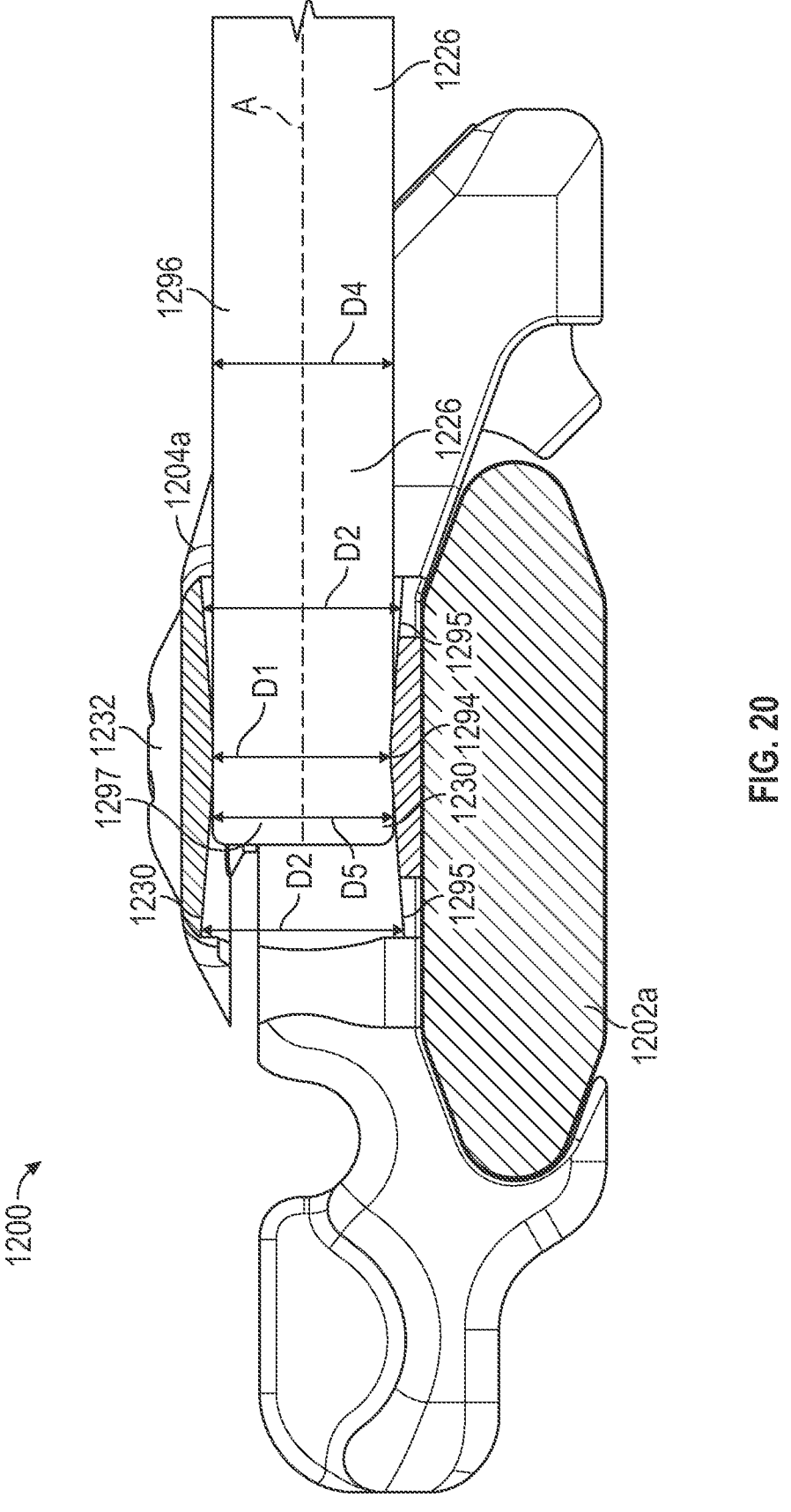
FIG. 20 illustrates a cross-sectional view of a portion of a pectus bar assembly.

FIG. 20 illustrates a cross-sectional view of a portion of the pectus bar assembly 1200. The pectus bar assembly 1200 of FIG. 20 can be consistent with FIGS. 12-19 discussed above. FIG. 20 shows how the bridge 1226 can interact with the slot 1230. More specifically, the slot 1230 can include a primary bore 1294 and angled portions 1295 where the primary bore 1294 can define a diameter D1 and the tapered portions can define a diameter D2 that is larger than the diameter D1. The angled portions 1295 can be tapered or angled and can extend from the primary bore 1294, which can be near a center of the slot 1230, towards respective ends of the slot 1230.

The bridge 1226 can include a shaft 1296 having a diameter D4 along a length of the shaft 1296, which can be a majority of a length of the bridge 1226. The bridge 1226 can also include a flared or enlarged portion 1297 located at an end of a shaft 1296. The bridge 1226 can include an enlarged portion at each of its ends. The enlarged portion 1297 can have or define a diameter D5 that is larger than a diameter D4 of the shaft 1296. This enlarged diameter can be slightly larger than the diameter D1 such that when the bridge 1226 moves through the slot 1230, there is some resistance to insertion or removal of the bridge 1226 into or from the slot 1230.

Also, because the diameters D2 can be larger than the diameter D4 of the shaft 1296 and because the diameter D1 can be only slightly larger than the diameter D4 of the shaft 1296, the bar links 1204 can be configured to tilt in multiple directions with respect to the longitudinal axis A of bridge 1226 even following insertion of the bridge 1226 into the slot 1230, when the arm actuator 1232 is in an unlocked configuration, which can allow the bar links 1204 to be placed at various angles with respect to the bar link 1204*a*.

When two pectus bars are used to correct a deformity, such as pectus excavatum, the bars (e.g., 1202) often do not perfectly align with each other (or are not parallel). The bars also may not be in the same plane and can be tilted or rotated with respect to each other. The features above allow the bar links 1204 to adapt to the misalignment between the two bars 1202. Also, these features (and optionally bending of the bridge 1226) can allow the bar links 1204 to be used with pectus bars installed in a crossing or X-configuration, or in other non-parallel configurations. When the bridge 1226 and bar link 1204*a* are in their desired positions, the arm actuator 1232 can be used to fix the orientation of the bridge 1226 with respect to the bar link 1204*a*.

This adjustability to tilt the bar links 1204 with respect to the bridge 1226 along with the bar links 1204 be adjustable along the pectus bars 1202, the bar links 1204 be adjustable along the bridge 1226, and the bar links 1204 be rotatable about the bridge 1226 allows for positioning or adjustability of the pectus bar assembly 1200 in every direction to allow for the pectus bar assembly 1200 to be installed in patient anatomy of a variety of shapes and sizes.

FIG. 21 illustrates an isometric view of a portion of a pectus bar assembly 2100. FIG. 22 illustrates an isometric view of a portion of a pectus bar assembly 2200. FIG. 23 illustrates an isometric view of a portion of a pectus bar assembly 2300. FIGS. 21-23 are discussed together below. The pectus bar assembly 2100, the pectus bar assembly 2200, and the pectus bar assembly 2300, can be similar to the pectus bar assembly 1200 discussed above. FIGS. 21-23 show different ways that the assemblies can be used.

As shown in FIG. 21, the pectus bar assembly 2100 can include two pectus bars 2102*a* and 2102*b*, two stabilizers 2104*a* and 2104*b*, and a single bridge 2226. As shown in FIG. 22, the pectus bar assembly 2200 can include three pectus bars, 2102*a* and 2102*b*, four stabilizers 2104*a*-2104*d*, and two bridge 2226*a* and 2226*b*. In this configuration, the bar 2102*b* can receive two stabilizers, 2104*b* and 2104*c* to connect the bars 2102*a* and 2102*c*. As shown in FIGS. 23, the pectus bar assembly 2300 can include three pectus bars, 2102*a* and 2102*b*, but only three stabilizers 2104*a*-2104*c*, and one bridge 2226, allowing for less hardware to be used to interconnect three pectus bars. FIGS. 21-23 thereby show that the pectus bar assembly 2200 can be used in systems using one or more pectus bars, such as 1, 2, 3, 4, 5, or the like.

Notes and Examples

The following, non-limiting examples, detail certain aspects of the present subject matter to solve the challenges and provide the benefits discussed herein, among others.

Example 1 is a pectus bar assembly comprising: a first pectus bar and a second pectus bar engageable with a sternum; a first bracket connectable to the first pectus bar; a second bracket connectable to the second pectus bar; and a bridge connectable to the first bracket and the second bracket to allow the first bracket and the first pectus bar to translate along the bridge, and to allow the second bracket and the second pectus bar to translate, independently of the first pectus bar, along the bridge.

In Example 2, the subject matter of Example 1 optionally includes the first bracket comprising: a base; and a receiver connected to the base, the receiver configured to receive an end portion of the first pectus bar therein.

In Example 3, the subject matter of Example 2 optionally includes wherein the first bracket includes a boss extending from a surface of the base, and wherein the bridge includes a slot configured to receive at least a portion of the boss therein.

In Example 4, the subject matter of Example 3 optionally includes wherein the boss is translatable within the slot to enable translation of the first bracket along the bridge.

In Example 5, the subject matter of Example 4 optionally includes a first fastener securable to the boss and engageable with the bridge to secure the first bracket to the bridge and to limit translation of the first bracket along the bridge.

In Example 6, the subject matter of Example 5 optionally includes the second bracket comprising: a base; and a receiver connected to the base, the receiver configured to receive an end portion of the second pectus bar therein.

In Example 7, the subject matter of Example 6 optionally includes wherein the second bracket includes a boss extending from a surface of the base, the boss translatable within the slot of the bridge to enable translation of the second bracket with respect to the bridge.

In Example 8, the subject matter of Example 7 optionally includes a second fastener securable to the boss of the second bracket and engageable with the bridge to secure the second bracket to the bridge and limit translation of the second bracket with respect to the bridge.

In Example 9, the subject matter of any one or more of Examples 1-8 optionally include the first bracket comprising: a base engageable with a first side of the bridge; and a plate securable to the base and engageable with a second side of the bridge, opposite the first side, the plate engageable with the first pectus bar, and the base and the plate together translatable along the bridge.

In Example 10, the subject matter of Example 9 optionally includes the first bracket comprising: a cap engageable with the first pectus bar and securable to the plate, wherein the cap, the plate, the base, and the bridge are together translatable along the first pectus bar.

In Example 11, the subject matter of Example 10 optionally includes the first bracket comprising: a fastener securable to the cap and the base to secure the first bracket to the first pectus bar and to limit translation of the cap, the plate, the base, and the bridge along the first pectus bar, and the fastener securable to the plate to limit translation of the base and the plate along the bridge.

In Example 12, the subject matter of Example 11 optionally includes the second bracket comprising: a base engageable with the first side of the bridge and engageable with the second pectus bar; a plate securable to the base and engageable with a second side of the bridge, opposite the first side, the base and the plate together translatable along the bridge;

a cap engageable with the second pectus bar and securable to the plate, wherein the cap, the plate, the base, and the bridge are together translatable along the second pectus bar; and a fastener securable to the cap and the base to secure the second bracket to the second pectus bar and to limit translation of the cap, the plate, the base, and the bridge along the second pectus bar, and the fastener securable to the plate to limit translation of the base and the plate along the bridge.

Example 13 is a pectus bar assembly comprising: a first pectus bar and a second pectus bar engageable with a sternum; a first bracket connectable to the first pectus bar and defining a receiver; and a second bracket connectable to the second pectus bar and including a projection, the projection insertable into the receiver to connect the first bracket to the second bracket and to secure the first pectus bar to the second pectus bar.

In Example 14, the subject matter of Example 13 optionally includes wherein the projection and the receiver together form a ratcheting interface to secure the first bracket to the second bracket.

In Example 15, the subject matter of any one or more of Examples 13-14 optionally include wherein the first bracket includes a pawl connected to the receiver, and wherein the projection includes a plurality of teeth, the plurality of teeth engageable with the pawl when the projection is inserted into the receiver to allow movement of the projection into the receiver and to limit movement of the projection out of the receiver.

In Example 16, the subject matter of any one or more of Examples 13-15 optionally include wherein the first bracket is translatable along the first pectus bar and wherein the second bracket is translatable along the second pectus bar.

In Example 17, the subject matter of Example 16 optionally includes a fastener securable to the first pectus bar and the first bracket to limit translation of the first bracket along the first pectus bar.

In Example 18, the subject matter of any one or more of Examples 13-17 optionally include wherein the projection is engageable with the receiver to limit movement of the second bracket and the second pectus bar toward the first bracket and the first pectus bar.

Example 19 is a method of installing a pectus bar assembly, the method comprising: inserting a first pectus bar and a second pectus bar into a sternum; connecting a first bracket to the first pectus bar; connecting a second bracket to the second pectus bar; connecting a bridge to the first bracket and the second bracket; translating the first bracket along the bridge; translating the second bracket along the bridge; fastening the first bracket to the bridge; and fastening the second bracket to the bridge.

In Example 20, the subject matter of Example 19 optionally includes fastening the first bracket to the first pectus bar; and fastening the second bracket to the second pectus bar.

In Example 21, the subject matter of any one or more of Examples 19-20 optionally include connecting a first cap to the first bracket; and translating the first bracket and the bridge along the first pectus bar.

In Example 22, the subject matter of Example 21 optionally includes connecting a second cap to the second bracket; and translating the second bracket and the bridge along the second pectus bar.

Example 23 is a pectus bar assembly comprising: a first pectus bar and a second pectus bar engageable with a sternum; a first bar link connectable to the first pectus bar and translatable along the first pectus bar; a second bar link connectable to the second pectus bar and translatable along the second pectus bar; and a bridge defining a longitudinal axis, the bridge connectable to the first bar link and the second bar link, the first bar link and the second bar link independently translatable along the bridge, and the first bar link and the second bar link independently rotatable about the longitudinal axis of the bridge.

In Example 24, the subject matter of Example 23 optionally includes the first bar link comprising: a body; and a shelf connected to the body, the shelf configured to receive a first end portion of the first pectus bar therein.

In Example 25, the subject matter of Example 24 optionally includes the first bar link comprising: an actuator extending through a bore of the body, the actuator operable between an unlocked position where the actuator is disengaged from the first pectus bar and a locked position where the actuator is engaged with a second end portion of the first pectus bar to cause engagement between the first end portion of the pectus bar and the shelf to secure the first bar link to the first pectus bar.

In Example 26, the subject matter of Example 25 optionally includes wherein the actuator is rotatable to cause the actuator to translate within the bore of the body.

In Example 27, the subject matter of Example 26 optionally includes wherein the actuator is captivated within the bore of the body.

In Example 28, the subject matter of any one or more of Examples 26-27 optionally include wherein a distal portion of the actuator is shaped to avoid engagement with an anterior portion of the first pectus bar when the actuator is moved from the unlocked position to the locked position.

In Example 29, the subject matter of any one or more of Examples 25-28 optionally include the first bar link comprising: a head extending away from the body and away from the actuator, the head movable to deform the body to release the first bar link from the first pectus bar.

In Example 30, the subject matter of Example 29 optionally includes wherein the head includes a rib graspable to manipulate the first bar link with respect to the bridge and the first pectus bar.

In Example 31, the subject matter of Example 30 optionally includes the first bar link comprising: an arm connected to the body, the arm and the body together defining a slot configured to receive the bridge at least partially therein; and an arm actuator connected to the body and the arm and operable to move between a first position where the bridge is movable with respect to the body and a second position where the arm and the body engage the bridge to secure the first bar link to the bridge.

In Example 32, the subject matter of Example 31 optionally includes wherein the arm and the body together form a clamp.

In Example 33, the subject matter of Example 32 optionally includes wherein the arm is connected to the body by a living hinge configured to allow the arm to elastically deflect with respect to the body when the arm moves between the first position and the second position.

In Example 34, the subject matter of Example 33 optionally includes wherein the slot is a bore including an angled portion at an opening of the bore configured to allow the first bar link to tilt with respect to the longitudinal axis of the bridge when the bridge is positioned in the slot of the first bar link and the arm actuator is in the first position.

In Example 35, the subject matter of any one or more of Examples 33-34 optionally include wherein the living hinge at least partially forms the slot.

In Example 36, the subject matter of any one or more of Examples 23-35 optionally include wherein the bridge is a cylindrical rod.

Example 37 is a pectus bar assembly comprising: a first pectus bar and a second pectus bar engageable with a sternum; a first bar link connectable to the first pectus bar and translatable along the first pectus bar; a second bar link connectable to the second pectus bar and translatable along the second pectus bar; and a rod extending along a longitudinal axis, the rod connectable to the first bar link and the second bar link, the first bar link and the second bar link independently translatable along the rod, and the first bar link and the second bar link independently rotatable about the longitudinal axis of the bridge.

In Example 38, the subject matter of Example 37 optionally includes the first bar link comprising: a body; and a shelf connected to the body, the shelf configured to receive a first end portion of the first pectus bar therein; and an actuator extending through a bore of the body, the actuator rotatable between an unlocked position where the actuator is disengaged from the first pectus bar and a locked position where the actuator is engaged with a second end portion of the first pectus bar to cause engagement between the first end portion of the pectus bar and the shelf to secure the first bar link to the first pectus bar.

In Example 39, the subject matter of Example 38 optionally includes wherein the actuator is captivated within the bore by the body.

In Example 40, the subject matter of any one or more of Examples 38-39 optionally include wherein a distal portion of the actuator is shaped to avoid engagement with an anterior portion of the first pectus bar when the actuator is moved from the unlocked position to the locked position.

In Example 41, the subject matter of any one or more of Examples 38-40 optionally include the first bar link comprising: a head extending away from the body and away from the actuator, the head movable to deform the body to release the first bar link from the first pectus bar.

In Example 42, the subject matter of Example 41 optionally includes the first bar link comprising: an arm connected to the body, the arm and the body together defining a slot configured to receive the bridge at least partially therein; and an arm actuator connected to the body and the arm and operable to move between a first position where the bridge is movable with respect to the body and a second position where the arm and the body engage the bridge to secure the first bar link to the bridge.

In Example 43, the apparatuses or method of any one or any combination of Examples 1-42 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A pectus bar assembly for correcting pectus excavatum or pectus carinatum, the pectus bar assembly comprising:
   a first pectus bar and a second pectus bar engageable with a sternum, the first pectus bar and the second pectus bar each configured to span across a sternum;
   a first bar link connectable to the first pectus bar and translatable along the first pectus bar;
   a second bar link connectable to the second pectus bar and translatable along the second pectus bar; and
   a bridge defining a longitudinal axis, the bridge connectable to the first bar link and the second bar link, the first bar link and the second bar link independently translatable along the bridge, and the first bar link and the second bar link independently rotatable about the longitudinal axis of the bridge.

2. The assembly of claim 1, the first bar link comprising:
   a body; and
   a shelf connected to the body, the shelf configured to receive a first end portion of the first pectus bar therein.

3. The assembly of claim 2, the first bar link comprising:

an actuator extending through a bore of the body, the actuator operable between an unlocked position where the actuator is disengaged from the first pectus bar and a locked position where the actuator is engaged with a second end portion of the first pectus bar to cause engagement between the first end portion of the pectus bar and the shelf to secure the first bar link to the first pectus bar.

4. The assembly of claim 3, wherein the actuator is rotatable to cause the actuator to translate within the bore of the body.

5. The assembly of claim 4, wherein the actuator is captivated within the bore of the body.

6. The assembly of claim 4, wherein a distal portion of the actuator is shaped to avoid engagement with an anterior portion of the first pectus bar when the actuator is moved from the unlocked position to the locked position.

7. The assembly of claim 3, the first bar link comprising:

a head extending away from the body and away from the actuator, the head movable to deform the body to release the first bar link from the first pectus bar.

8. The assembly of claim 7, wherein the head includes a rib graspable to manipulate the first bar link with respect to the bridge and the first pectus bar.

9. The assembly of claim 8, the first bar link comprising:

an arm connected to the body, the arm and the body together defining a slot configured to receive the bridge at least partially therein; and an arm actuator connected to the body and the arm and operable to move between a first position where the bridge is movable with respect to the body and a second position where the arm and the body engage the bridge to secure the first bar link to the bridge.

10. The assembly of claim 9, wherein the arm and the body together form a clamp.

11. The assembly of claim 10, wherein the arm is connected to the body by a living hinge configured to allow the arm to elastically deflect with respect to the body when the arm actuator moves between the first position and the second position.

12. The assembly of claim 11, wherein the slot is a bore including an angled portion at an opening of the bore configured to allow the first bar link to tilt with respect to the longitudinal axis of the bridge when the bridge is positioned in the slot of the first bar link and the arm actuator is in the first position.

13. The assembly of claim 11, wherein the living hinge at least partially forms the slot.

14. The assembly of claim 1, wherein the bridge is a cylindrical rod.

15. A pectus bar assembly for correcting pectus excavatum or pectus carinatum, the pectus bar assembly comprising:

a first pectus bar and a second pectus bar engageable with a sternum, the first pectus bar and the second pectus bar each configured to span across a sternum;

a first bar link connectable to the first pectus bar and translatable along the first pectus bar;

a second bar link connectable to the second pectus bar and translatable along the second pectus bar; and a rod extending along a longitudinal axis, the rod connectable to the first bar link and the second bar link, the first bar link and the second bar link independently translatable along the rod, and the first bar link and the second bar link independently rotatable about the longitudinal axis of the rod.

16. The assembly of claim 15, the first bar link comprising:

a body;

a shelf connected to the body, the shelf configured to receive a first end portion of the first pectus bar therein; and an actuator extending through a bore of the body, the actuator rotatable between an unlocked position where the actuator is disengaged from the first pectus bar and a locked position where the actuator is engaged with a second end portion of the first pectus bar to cause engagement between the first end portion of the pectus bar and the shelf to secure the first bar link to the first pectus bar.

17. The assembly of claim 16, wherein the actuator is captivated within the bore by the body.

18. The assembly of claim 16, wherein a distal portion of the actuator is shaped to avoid engagement with an anterior portion of the first pectus bar when the actuator is moved from the unlocked position to the locked position.

19. The assembly of claim 16, the first bar link comprising:

a head extending away from the body and away from the actuator, the head movable to deform the body to release the first bar link from the first pectus bar.

20. The assembly of claim 19, the first bar link comprising:

an arm connected to the body, the arm and the body together defining a slot configured to receive the rod at least partially therein; and an arm actuator connected to the body and the arm and operable to move between a first position where the rod is movable with respect to the body and a second position where the arm and the body engage the rod to secure the first bar link to the rod.

* * * * *